United States Patent
Taylor et al.

(10) Patent No.: US 12,226,340 B2
(45) Date of Patent: *Feb. 18, 2025

(54) THERMAL SYSTEM WITH OVERSHOOT REDUCTION

(71) Applicant: Stryker Corporation, Kalamazoo, MI (US)

(72) Inventors: Gregory S. Taylor, Kalamazoo, MI (US); Marko N. Kostic, Oshawa (CA); Christopher John Hopper, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 106 days.

This patent is subject to a terminal disclaimer.

(21) Appl. No.: 18/080,341

(22) Filed: Dec. 13, 2022

(65) Prior Publication Data

US 2023/0111328 A1     Apr. 13, 2023

Related U.S. Application Data

(63) Continuation of application No. 16/218,883, filed on Dec. 13, 2018, now Pat. No. 11,554,039.

(Continued)

(51) Int. Cl.
*A61F 7/00* (2006.01)
*A61B 5/00* (2006.01)
(Continued)

(52) U.S. Cl.
CPC .............. *A61F 7/0085* (2013.01); *A61B 5/01* (2013.01); *A61B 5/015* (2013.01); *A61B 5/486* (2013.01); *A61B 18/02* (2013.01); *A61F 7/02* (2013.01); *A61B 5/7425* (2013.01); *A61B 2017/00084* (2013.01); *A61B 2018/0237* (2013.01);

(Continued)

(58) Field of Classification Search
CPC .......... A61B 18/02; A61B 2017/00084; A61B 2018/0237; A61B 2505/09; A61B 5/01; A61B 5/015; A61B 5/486; A61B 5/7425; A61F 2007/0001; A61F 2007/0054; A61F 2007/0056; A61F 2007/0076; A61F 2007/0086; A61F 2007/0093;
(Continued)

(56) References Cited

U.S. PATENT DOCUMENTS

2008/0228245 A1* 9/2008 Schock ................... A61F 7/00
607/104

* cited by examiner

*Primary Examiner* — Tigist S Demie
(74) *Attorney, Agent, or Firm* — Warner Norcross + Judd LLP

(57) ABSTRACT

A thermal control unit for controlling a patient's temperature includes a fluid outlet for delivering temperature-controlled fluid to a patient, a pump, a heat exchanger, and a controller that automatically pauses thermal treatment of the patient prior the patient reaching a target temperature. During the pause, the controller assesses a reaction of the patient and changes a temperature of the fluid only inside the thermal control unit if the patient is likely to reach the target temperature without further thermal treatment. However, if the patient is unlikely to reach the target temperature without further thermal treatment, the controller restarts the thermal treatment. The controller may pause thermal treatment again prior to reaching the target temperature and assess the patient's reaction. In some embodiments, the controller may selectively include and exclude a fluid reservoir in a circulation channel within the thermal control unit.

18 Claims, 12 Drawing Sheets

Related U.S. Application Data

(60) Provisional application No. 62/610,319, filed on Dec. 26, 2017.

(51) Int. Cl.
  *A61B 5/01* (2006.01)
  *A61B 18/00* (2006.01)
  *A61B 18/02* (2006.01)
  *A61F 7/02* (2006.01)
  *A61B 17/00* (2006.01)

(52) U.S. Cl.
  CPC ... *A61B 2505/09* (2013.01); *A61F 2007/0001* (2013.01); *A61F 2007/0054* (2013.01); *A61F 2007/0056* (2013.01); *A61F 2007/0076* (2013.01); *A61F 2007/0086* (2013.01); *A61F 2007/0093* (2013.01); *A61F 2007/0095* (2013.01); *A61F 2007/0288* (2013.01); *A61F 2007/0295* (2013.01)

(58) Field of Classification Search
  CPC ...... A61F 2007/0095; A61F 2007/0288; A61F 2007/0295; A61F 7/0085; A61F 7/02
  See application file for complete search history.

$T_1$ Waterflow is turned off @ $T_a$ in order to check impact on slope of $T_P$ $T_2$ $T_P \downarrow$ not shown to change so waterflow restricted to internal and water circulates internally and is 100% heated $T_3$ Once $T_W$ reaches $T_P + 1.0°C$ then waterflow is opened back up to pads and continued to warm to $40°C$ until overshoot is prevented or stopped

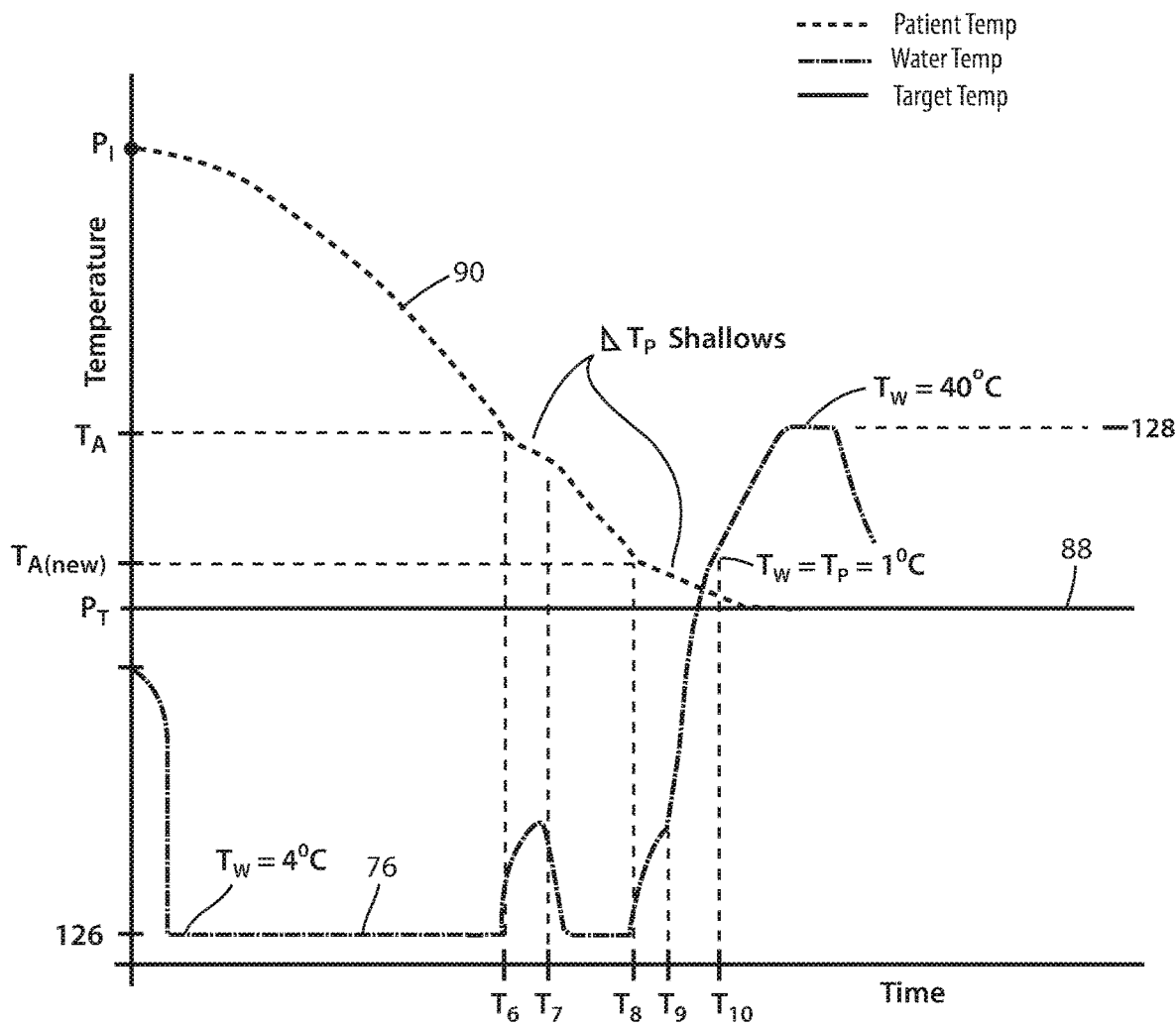

$T_6$ Waterflow is turned off @ $T_a$ in order to check impact on slope of $T_P$ $T_7$ $T_P \downarrow$ is shown to change so waterflow is turned back on externally and set to cooling $T_8$ Waterflow is turned off @ $T_a$ in order to check impact on stop of $T_P$ $T_9$ Algorithm determines $T_P$ is close enough to target to warm $T_W$ internally to $T_P + 1.0°C$ $T_{10}$ TW @ $T_P + 1°C$ and turned to external waterflow to pads to warm $T_P$

FIG. 7

THERMAL SYSTEM WITH OVERSHOOT REDUCTION

CROSS-REFERENCE TO RELATED APPLICATIONS

This application claims priority to U.S. patent application Ser. No. 16/218,883 filed Dec. 13, 2018, by inventors Gregory S. Taylor et al. and entitled THERMAL SYSTEM WITH OVERSHOOT REDUCTION, which in turn claims priority to U.S. provisional patent application Ser. No. 62/610,319 filed Dec. 26, 2017, by inventors Gregory S. Taylor et al. and entitled THERMAL SYSTEM WITH OVERSHOOT REDUCTION, the complete disclosures of both of which are incorporated herein by reference.

BACKGROUND

The present disclosure relates to a thermal control system for controlling the temperature of circulating fluid that is delivered to one or more thermal pads positioned in contact with a patient.

Thermal control systems are known in the art for controlling the temperature of a patient by providing a thermal control unit that supplies temperature-controlled fluid to one or more thermal pads or catheters positioned in contact with a patient. The thermal control unit includes one or more heat exchangers for controlling the temperature of the fluid and a pump that pumps the temperature-controlled fluid to the pad(s) and/or catheter. After passing through the pad(s) and/or catheter, the fluid is returned to the thermal control unit where any necessary adjustments to the temperature of the returning fluid are made before being pumped back to the pad(s) and/or catheter. In some instances, the temperature of the fluid is controlled to a static target temperature, while in other instances the temperature of the fluid is varied as necessary in order to automatically effectuate a target patient temperature.

The thermal control unit can be used to warm or cool a patient, and it is often desirable to heat or cool the patient to a target temperature relatively quickly. However, it is also often desirable to heat or cool the patient to a target temperature without overshooting the target temperature.

SUMMARY

The present disclosure is directed to an improved thermal control unit that brings the patient's temperature to a target temperature in an expeditious manner while also simultaneously reducing any overshoot in the patient's temperature. By reducing such overshoot, the magnitude of oscillations in the patient's temperature above and below a target temperature may also be reduced, thereby enabling the patient's temperature to be maintained within a tighter range of the target temperature. In other aspects, the rate at which the temperature of the fluid circulating within the thermal control unit can be increased by selectively including and excluding a fluid reservoir in a circulation channel within the thermal control unit. Still further, in other aspects, the ease of carrying out disinfection of the thermal control unit, including a fluid reservoir, may be improved. Still other improved aspects of the thermal control system disclosed herein will be apparent to those skilled in the art in light of the following written description.

According to one embodiment of the present disclosure a thermal control unit is provided for controlling a patient's temperature that includes a fluid outlet, a fluid inlet, a circulation channel, a pump, a heat exchanger, a fluid temperature sensor, a patient temperature probe port, a user interface, and a controller. The circulation channel is fluidly coupled to the fluid outlet and fluid inlet. The pump circulates fluid through the circulation channel from the fluid inlet to the fluid outlet and out of the fluid outlet. The heat exchanger adds or removes heat from the fluid circulating in the circulation channel when the heat exchanger is activated. The fluid temperature sensor senses a temperature of the circulating fluid. The patient temperature probe port receives patient temperature readings from a patient temperature probe. The user interface receives a patient target temperature, and the controller stops a flow of fluid out of the fluid outlet prior to the patient temperature reaching the patient target temperature.

According to other aspects of the present disclosure, the controller monitors a slope of the patient temperature readings after the flow of fluid out of the fluid outlet is stopped. The monitoring may continue for a predefined time period. If the slope of the patient temperature readings changes by more than a threshold during the predefined time period, the controller restarts the flow of fluid out of the fluid outlet after the predefined time period. If the slope of the patient temperature readings does not change by more than a threshold during the predefined time period, the controller activates the pump and closes a valve such that the fluid circulates within the circulation channel of the thermal control unit but does not flow out of the fluid outlet.

The controller may activate the heat exchanger while the valve is closed until the temperature of the fluid reaches a specific temperature. The specific temperature may have a predefined relationship to a temperature of the patient, and the controller may open the valve after the temperature of the fluid reaches the specific temperature.

After restarting the flow of fluid out of the fluid outlet, the controller re-stops the flow of fluid out of the fluid outlet after the patient temperature has moved toward the patient target temperature but prior to the patient temperature reaching the patient target temperature.

In some embodiments, the controller stops the flow of fluid out of the fluid outlet by closing a valve to the fluid outlet, and the controller continues to activate the pump such that fluid is pumped internally within the circulation channel while the flow of fluid out of the fluid outlet is stopped. In other embodiments, the controller may stop the flow of fluid out of the fluid outlet by deactivating the pump.

According to another embodiment, a thermal control unit for controlling a patient's temperature is provided that includes a fluid outlet, a fluid inlet, a circulation channel, a pump, a heat exchanger, a fluid temperature sensor, a patient temperature probe port, a user interface, and a controller. The pump circulates fluid through the circulation channel from the fluid inlet to the fluid outlet and out of the fluid outlet. The heat exchanger adds or removes heat from the fluid circulating in the circulation channel when activated. The fluid temperature sensor senses a temperature of the circulating fluid. The patient temperature probe port receives patient temperature readings from a patient temperature probe. The user interface receives a patient target temperature, and the controller communicates with the temperature probe port, the pump, the fluid temperature sensor, and the user interface. The controller is adapted to deactivate the heat exchanger prior to the patient temperature reaching the patient target temperature such that the heat exchanger does not actively add heat to, or remove heat from, the circulating fluid.

After deactivating the heat exchanger, the controller monitors a slope of the patient temperature readings for a predefined time period. The controller reactivates the heat exchanger after the predefined time period if the slope of the patient temperature readings changes by more than a threshold. Thereafter, the controller may once again deactivate the heat exchanger after the patient temperature has moved toward the patient target temperature but prior to the patient temperature reaching the patient target temperature.

If the slope of the patient temperature readings does not change by more than a threshold during the predefined time period, the controller, in some embodiments, activates the pump and closes a valve such that the fluid circulates within the circulation channel of the thermal control unit but does not flow out of the fluid outlet. The controller may reactivate the heat exchanger while the valve is closed until the temperature of the fluid reaches a specific temperature. The controller opens the valve after the temperature of the fluid reaches the specific temperature.

According to another embodiment of the present disclosure, a thermal control unit for controlling a patient's temperature is provided. The thermal control unit includes a fluid outlet, a fluid inlet, a circulation channel, a pump, a heat exchanger, a fluid temperature sensor, a patient temperature probe port, a user interface, and a controller. The pump circulates fluid through the circulation channel from the fluid inlet to the fluid outlet and out of the fluid outlet. The heat exchanger adds or removes heat from the fluid circulating in the circulation channel when activated. The fluid temperature sensor senses a temperature of the circulating fluid. The patient temperature probe port receives patient temperature readings from a patient temperature probe. The user interface receives a patient target temperature, and the controller communicates with the temperature probe port, the pump, the fluid temperature sensor, and the user interface. The controller is adapted to vary both a flow and temperature of the fluid exiting the fluid outlet in order to automatically bring the patient to the patient target temperature.

In some embodiments, the controller reduces a flow of the fluid out of the fluid outlet prior to the patient temperature reaching the patient target temperature.

In some embodiments, the heat exchanger includes a compressor and the controller is further adapted to vary a speed of the compressor in order to automatically bring the patient to the patient target temperature.

The controller may be adapted to vary a flow of the fluid exiting the fluid outlet by reducing the fluid flow or completely stopping the flow of fluid out of the fluid outlet.

When stopping the fluid flow, the controller may monitor a slope of the patient temperature readings for a predefined time period and (1) if the slope of the patient temperature readings changes by more than a threshold during the predefined time period, the controller restarts the flow of fluid out of the fluid outlet; and (2) if the slope of the patient temperature readings does not change by more than the threshold during the predefined time period, the controller activates the pump and closes a valve such that the fluid circulates within the circulation channel of the thermal control unit but does not flow out of the fluid outlet.

In some embodiments, the thermal control unit includes a fluid reservoir and a valve adapted to selectively include and exclude the fluid reservoir to and from the circulation channel. The controller is adapted to control the valve in order to automatically bring the patient to the patient target temperature.

According to another embodiment of the present disclosure, a thermal control unit for controlling a patient's temperature is provided. The thermal control unit includes a fluid outlet, a fluid inlet, a circulation channel, a pump, a heat exchanger, a fluid reservoir, a valve, and a controller. The pump circulates fluid through the circulation channel from the fluid inlet to the fluid outlet and out of the fluid outlet. The heat exchanger adds or removes heat from the fluid circulating in the circulation channel when activated. The fluid reservoir supplies fluid to the circulation channel. The valve selectively includes the fluid reservoir in the circulation channel and selectively excludes the fluid reservoir from the circulation channel. When the reservoir is included in the circulation channel, the circulating fluid flows through the reservoir. When the reservoir is excluded from the circulation channel, the fluid flows around the reservoir. The controller communicates with the pump, the heat exchanger, and the valve, and the controller is adapted to control the valve and the heat exchanger in order to automatically bring the patient to a patient target temperature.

According to other aspects of the disclosure, the controller controls the valve such that the fluid reservoir is included in the circulation channel when the thermal control unit is being disinfected.

The controller, in some embodiments, controls the valve in combination with the heat exchanger in order to automatically bring the patient to the patient target temperature.

In some embodiments, the controller controls the valve to exclude the fluid reservoir from the circulation channel for an initial period during which the patient temperature readings approach, but do not reach, the patient target temperature. During a subsequent time period, the controller controls the valve to include the fluid reservoir in the circulation channel. The subsequent period may commence prior to the patient reaching the patient target temperature.

The controller is configured in some embodiments to control the valve such that the fluid reservoir is included in the circulation channel when a quick increase in the temperature of the circulating fluid will reduce overshoot of the patient temperature readings past the patient target temperature.

According to another embodiment of the present disclosure, a thermal control unit for controlling a patient's temperature is provided. The thermal control unit includes a fluid outlet, a fluid inlet, a circulation channel, a pump, a heat exchanger, and a controller. The pump circulates fluid through the circulation channel from the fluid inlet to the fluid outlet and out of the fluid outlet. The heat exchanger adds or removes heat from the fluid circulating in the circulation channel when activated. The fluid reservoir supplies fluid to the circulation channel. The controller communicates with the pump and heat exchanger and controls the heat exchanger to cool the patient to a target patient temperature. The controller is further adapted to automatically pause the cooling of the patient prior to the patient reaching the target patient temperature and assess a reaction of the patient to the paused cooling. The controller is still further adapted to warm the circulating fluid internally within the thermal control unit if the reaction indicates the patient will likely reach the target patient temperature without further cooling by the thermal control unit and to restart cooling of the patient if the reaction of the patient indicates the patient will likely not reach the target patient temperature without further cooling by the thermal control unit.

The pause in the cooling of the patient may be implemented by any one or more of the following: deactivating the pump; keeping the pump activated while closing a valve such that fluid does not exit out of the fluid outlet; and/or deactivating the heat exchanger.

In some embodiments, the thermal control unit includes a fluid reservoir adapted to supply fluid to the circulation channel and a valve adapted to selectively include the fluid reservoir in the circulation channel and selectively exclude the fluid reservoir from the circulation channel. The fluid flows through the reservoir when the reservoir is included in the circulation channel and the fluid flows around the reservoir when the fluid reservoir is excluded from the circulation channel.

The controller may control the valve such that the fluid reservoir is excluded from the circulation channel during cooling of the patient.

The controller may control the valve such that the fluid reservoir is included in the circulation channel when the controller warms the circulating fluid internally within the thermal control unit. The controller, in some embodiments, includes the fluid reservoir in the circulation channel for a predefined period when warming the circulation fluid internally within the thermal control unit and, after the expiration of the predefined period, excludes the fluid reservoir from the circulation channel. The predefined period may be set equal to an amount of time it takes to pump a volume of fluid through the fluid reservoir substantially equal to the volume of the fluid that was contained within the fluid reservoir immediately prior to the fluid reservoir being included in the circulation channel. In this manner, the fluid reservoir is included in the circulation channel for a length of time sufficient to allow the fluid it contained prior to being included in the circulation channel to be added to the circulation channel.

In some embodiments, the controller controls the heat exchanger using first and second control loop feedback mechanisms. The first control loop feedback mechanism uses a first set of coefficients and an error value, and the second control loop feedback mechanism uses a second set of coefficients and the error value. The error value is defined as a difference between a current patient temperature reading and the patient target temperature.

According to another embodiment of the present disclosure, a thermal control unit is provided for controlling a patient's temperature that includes a fluid outlet, a fluid inlet, a circulation channel, a pump, a heat exchanger, a fluid temperature sensor, a patient temperature probe port, a user interface, and a controller. The circulation channel is fluidly coupled to the fluid outlet and fluid inlet. The pump circulates fluid through the circulation channel from the fluid inlet to the fluid outlet and out of the fluid outlet. The heat exchanger adds or removes heat from the fluid circulating in the circulation channel when the heat exchanger is activated. The fluid temperature sensor senses a temperature of the circulating fluid. The patient temperature probe port receives patient temperature readings from a patient temperature probe. The user interface receives a patient target temperature and the controller communicates with the temperature probe port, the pump, the heat exchanger, the fluid temperature sensor, and the user interface. The controller controls the heat exchanger to bring the patient to the patient target temperature using first and second control loop feedback mechanisms. The first control loop feedback mechanism uses a first set of coefficients and an error value, and the second control loop feedback mechanism uses a second set of coefficients and the error value. The error value is defined as a difference between a current patient temperature reading and the patient target temperature.

In some of the aforementioned embodiments, the first control loop feedback mechanism includes first proportional, first integral, and first derivative control terms, each of which is multiplied by a coefficient from the first set of coefficients; and the second control loop feedback mechanism includes second proportional, second integral, and second derivative control terms, each of which is multiplied by a coefficient from the second set of coefficients. In still other embodiments, the set of coefficients includes fewer than three coefficients.

The controller switches from using the first control loop feedback mechanism to using the second control loop feedback mechanism at a transition point. The transition point occurs prior to the patient reaching the patient target temperature in some embodiments. In other embodiments, the transition point occurs after the patient reaches the patient target temperature.

In still other embodiments, the controller is further adapted to control the heat exchanger to bring the patient to the patient target temperature using a third control loop feedback mechanism. The third control loop feedback mechanism uses a third set of coefficients and the error value. The controller switches from using the second control loop feedback mechanism to using the third control loop feedback mechanism at a second transition point. The second transition point occurs after first transition point.

In any of the embodiments disclosed herein, the fluid reservoir may be thermally isolated from the heat exchanger when the fluid reservoir is not in the circulation channel, thereby allowing the fluid in the reservoir to have a different temperature than the fluid in the circulation channel. When the fluid reservoir is brought into the circulation channel, the fluid from the reservoir mixes with the fluid in the circulation channel and the temperature of the circulating fluid is changed based on the temperature of the fluid from the reservoir and the volume of fluid that exits from the reservoir and into the circulation channel.

Before the various embodiments disclosed herein are explained in detail, it is to be understood that the claims are not to be limited to the details of operation or to the details of construction, nor to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 7 is a graph of a patient target temperature, patient measured temperature, and fluid temperature illustrating a second example of the temperature control algorithm of FIG. 5;

DETAILED DESCRIPTION OF THE EMBODIMENTS

Figure 1:
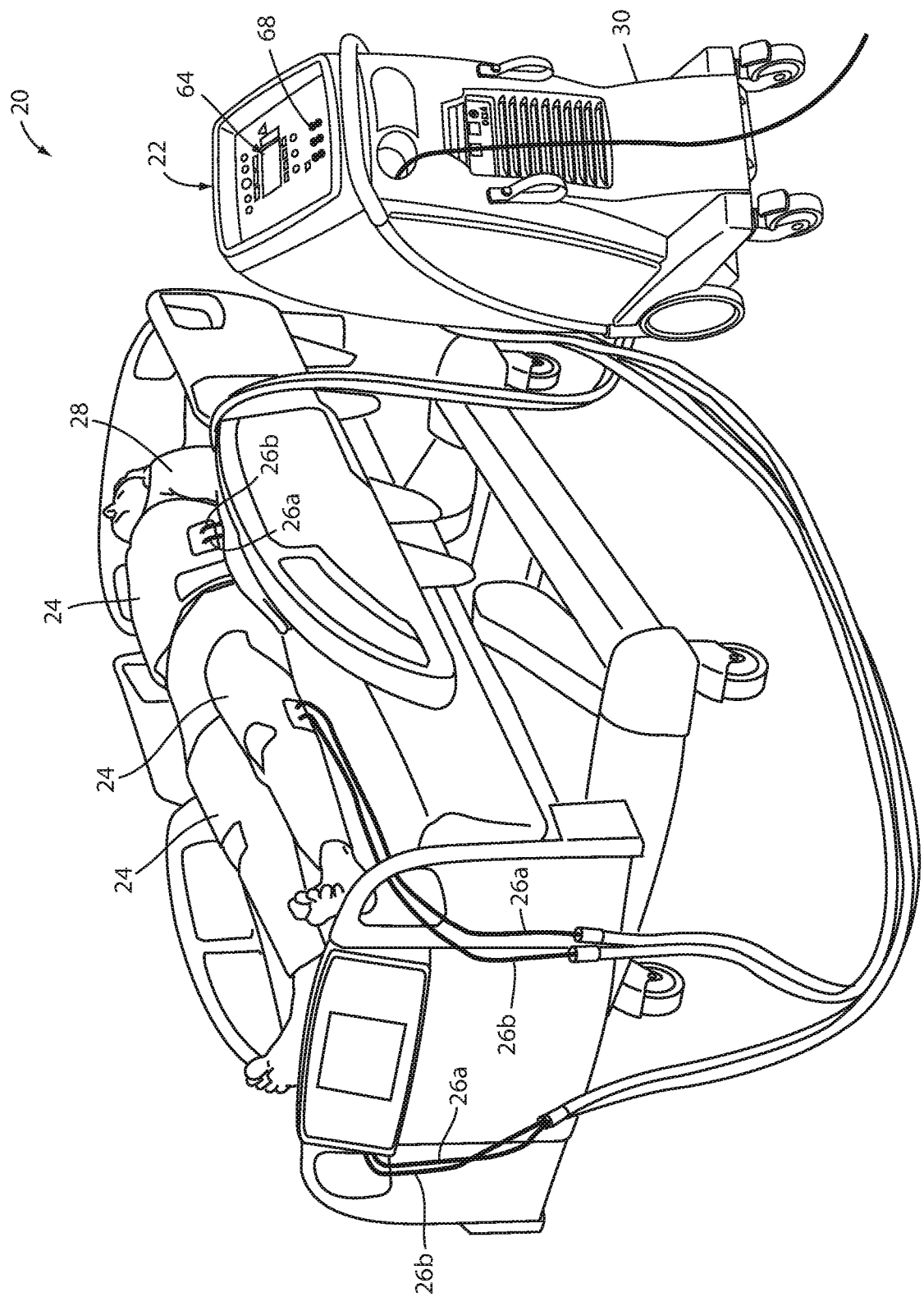
FIG. 1 is a perspective view of a thermal control system according to one aspect of the present disclosure shown applied to a patient on a patient support apparatus.

A thermal control system 20 according to one embodiment of the present disclosure is shown in FIG. 1. Thermal control system 20 is adapted to control the temperature of a patient 28, which may involve raising, lowering, and/or maintaining the patient's temperature. Thermal control system 20 includes a thermal control unit 22 coupled to one or more thermal therapy devices 24. The thermal therapy devices 24 are illustrated in FIG. 1 to be thermal pads, but it will be understood that thermal therapy devices 24 may take on other forms, such as, but not limited to, blankets, vests, patches, caps, catheters, or other structures that receive temperature-controlled fluid. For purposes of the following written description, thermal therapy devices 24 will be referred to as thermal pads 24, but it will be understood by those skilled in the art that this terminology is used merely for convenience and that the phrase "thermal pad" is intended to cover all of the different variations of thermal therapy devices 24 mentioned above (e.g. blankets, vests, patches, caps, catheters, etc.) and variations thereof.

Thermal control unit 22 is coupled to thermal pads 24 via a plurality of hoses 26. Thermal control unit 22 delivers temperature-controlled fluid (such as, but not limited to, water or a water mixture) to the thermal pads 24 via the fluid supply hoses 26a. After the temperature-controlled fluid has passed through thermal pads 24, thermal control unit 22 receives the temperature-controlled fluid back from thermal pads 24 via the return hoses 26b.

In the embodiment of thermal control system 20 shown in FIG. 1, three thermal pads 24 are used in the treatment of patient 28. A first thermal pad 24 is wrapped around a patient's torso, while second and third thermal pads 24 are wrapped, respectively, around the patient's right and left legs. Other configurations can be used and different numbers of thermal pads 24 may be used with thermal control unit 22, depending upon the number of inlet and outlet ports that are included with thermal control unit 22. By controlling the temperature of the fluid delivered to thermal pads 24 via supply hoses 26a, the temperature of the patient 28 can be controlled via the close contact of the pads 24 with the patient 28 and the resultant heat transfer therebetween.

Figure 2:
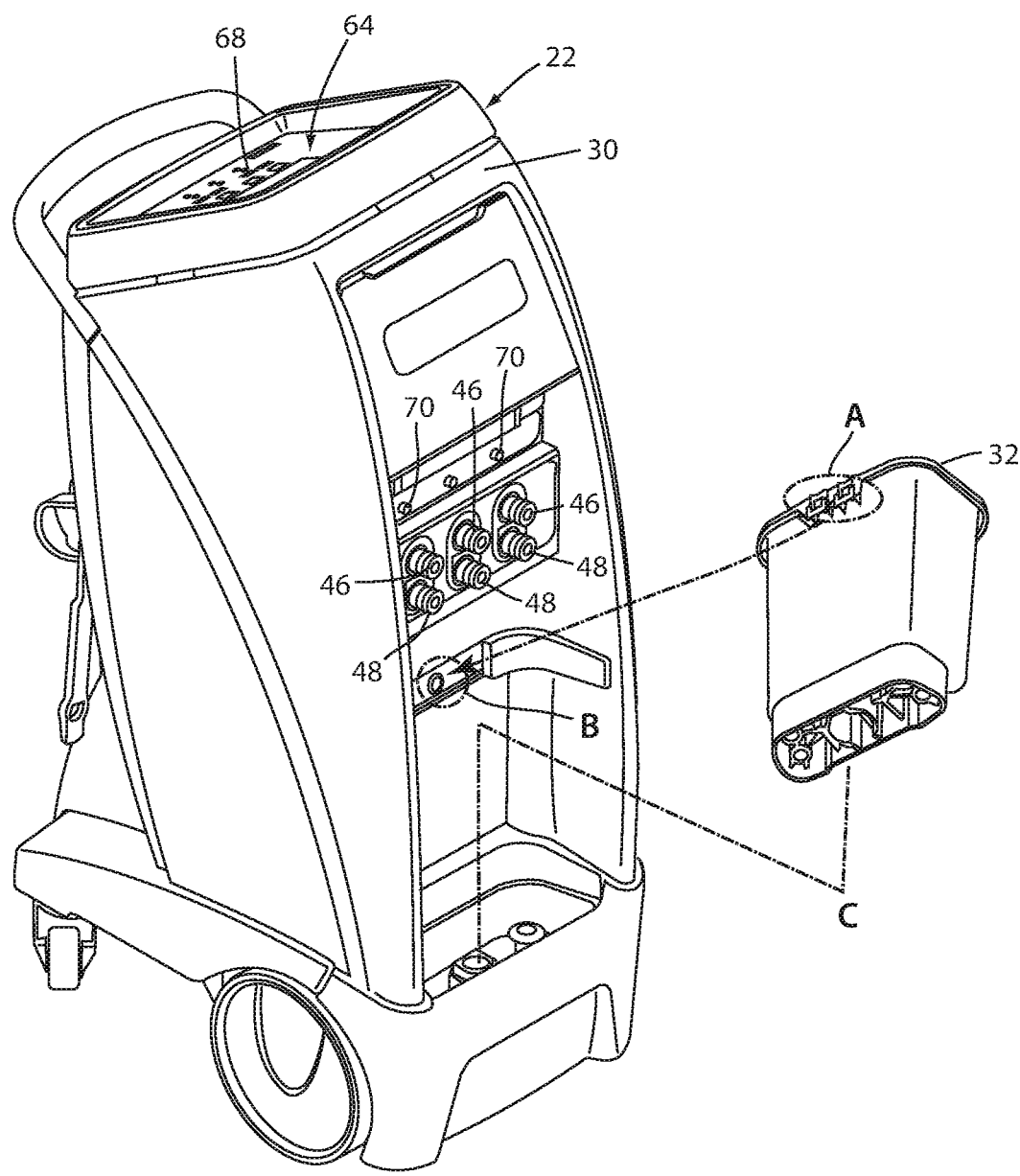
FIG. 2 is a perspective view of a thermal control unit of the thermal control system of FIG. 1.

As shown more clearly in FIG. 2, thermal control unit 22 includes a main body 30 to which a removable reservoir 32 may be coupled and uncoupled. Removable reservoir 32 is configured to hold the fluid that is to be circulated through control unit 22 and the one or more thermal pads 24. By being removable from thermal control unit 22, reservoir 32 can be easily carried to a sink or faucet for filling and/or dumping of the water or other fluid. This allows users of thermal control system 20 to more easily fill control unit 22 prior to its use, as well as to drain unit 22 after use.

Figure 3:
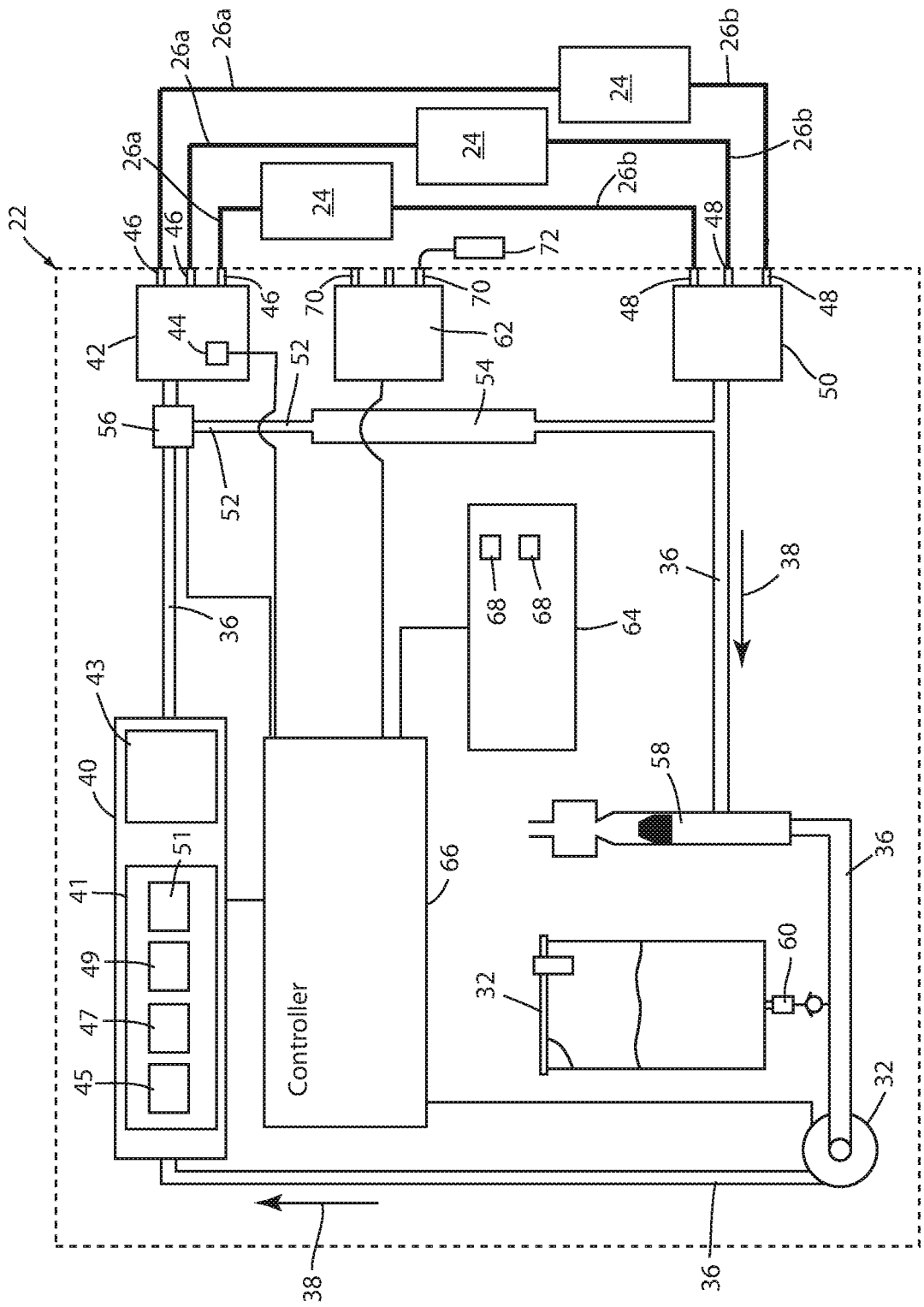
FIG. 3 is a block diagram of a first embodiment of the thermal control unit of FIG. 2.

As shown in FIG. 3, thermal control unit 22 includes a pump 34 for circulating fluid through a circulation channel 36. Pump 34, when activated, circulates the fluid through circulation channel 36 in the direction of arrows 38 (clockwise in FIG. 3). Starting at pump 34 the circulating fluid first passes through a heat exchanger 40 that adjusts, as necessary, the temperature of the circulating fluid. Heat exchanger 40 may take on a variety of different forms. In some embodiments, heat exchanger 40 is a thermoelectric heater and cooler. In the embodiment shown in FIG. 3, heat exchanger 40 includes a chiller 41 and a heater 43. Further, in the embodiment shown in FIG. 3, chiller 41 is a conventional vapor-compression refrigeration unit having a compressor 45, a condenser 47, an evaporator 49, an expansion valve (not shown), and a fan 51 for removing heat from the condenser. Other types of chillers and/or heaters may be used.

After passing through heat exchanger 40, the circulating fluid is delivered to an outlet manifold 42 having an outlet temperature sensor 44 and a plurality of outlet ports 46. Temperature sensor 44 is adapted to detect a temperature of the fluid inside of outlet manifold 42 and report it to a controller 66. Outlet ports 46 are coupled to supply hoses 26a. Supply hoses 26a are coupled, in turn, to thermal pads 24 and deliver temperature-controlled fluid to the thermal pads 24. The temperature-controlled fluid, after passing through the thermal pads 24, is returned to thermal control unit 22 via return hoses 26b. Return hoses 26b couple to a plurality of inlet ports 48. Inlet ports 48 are fluidly coupled to an inlet manifold 50 inside of thermal control unit 22.

Control unit 22 also includes a bypass line 52 fluidly coupled to outlet manifold 42 and inlet manifold 50 (FIG. 3). Bypass line 52 allows fluid to circulate through circulation channel 36 even in the absence of any thermal pads 24 or hoses 26a being coupled to any of outlet ports 46. In the illustrated embodiment, bypass line 52 includes an optional filter 54 that is adapted to filter the circulating fluid. If included, filter 54 may be a particle filter adapted to filter out particles within the circulating fluid that exceed a size threshold, or filter 54 may be a biological filter adapted to purify or sanitize the circulating fluid, or it may be a combination of both. In some embodiments, filter 54 is constructed and/or positioned within thermal control unit 22 in any of the manners disclosed in commonly assigned U.S. patent application Ser. No. 62/404,676 filed Oct. 11, 2016, by inventors Marko Kostic et al. and entitled THERMAL CONTROL SYSTEM, the complete disclosure of which is incorporated herein by reference.

The flow of fluid through bypass line 52 is controllable by way of a bypass valve 56 positioned at the intersection of bypass line 52 and outlet manifold 42 (FIG. 3). When open, bypass valve 56 allows fluid to flow through circulation channel 36 to outlet manifold 42, and from outlet manifold 42 to the connected thermal pads 24. When closed, bypass valve 56 stops fluid from flowing to outlet manifold 42 (and thermal pads 24) and instead diverts the fluid flow along bypass line 52. In some embodiments, bypass valve 56 may be controllable such that selective portions of the fluid are directed to outlet manifold 42 and along bypass line 52. As will be discussed in more detail below, the stopping of fluid flow to thermal pads 24 via bypass valve 56 may occur during the thermal treatment of a patient, as well as at other times.

The incoming fluid flowing into inlet manifold 50 from inlet ports 48 and/or bypass line 52 travels back toward pump 34 and into an air remover 58. Air remover 58 includes any structure in which the flow of fluid slows down sufficiently to allow air bubbles contained within the circulating fluid to float upwardly and escape to the ambient surroundings. In some embodiments, air remover 58 is constructed in accordance with any of the configurations disclosed in commonly assigned U.S. patent application Ser. No. 15/646,847 filed Jul. 11, 2017, by inventor Gregory S. Taylor and entitled THERMAL CONTROL SYSTEM, the complete disclosure of which is hereby incorporated herein by reference. After passing through air remover 58, the circulating fluid flows past a valve 60 positioned beneath fluid reservoir 32. Fluid reservoir 32 supplies fluid to thermal control unit 22 and circulation channel 36 via valve 60, which may be a conventional check valve, or other type of valve, that automatically opens when reservoir 32 is coupled to thermal control unit 22 and that automatically closes when reservoir 32 is decoupled from thermal control unit 22 (see FIG. 2). After passing by valve 60, the circulating fluid travels to pump 34 and the circuit is repeated.

Controller 66 of thermal control unit 22 is contained within main body 30 of thermal control unit 22 and is in electrical communication with pump 34, heat exchanger 40, outlet temperature sensor 44, bypass valve 56, a patient temperature module 62, and a user interface 64. Controller 66 includes any and all electrical circuitry and components necessary to carry out the functions and algorithms described herein, as would be known to one of ordinary skill in the art. Generally speaking, controller 66 may include one or more microcontrollers, microprocessors, and/or other programmable electronics that are programmed to carry out the functions described herein. It will be understood that controller 66 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions in thermal control unit 22, or they may reside in a common location within thermal control unit 22. When physically distributed, the components may communicate using any suitable serial or parallel communication protocol, such as, but not limited to, CAN, LIN, Firewire, I-squared-C, RS-232, RS-465, universal serial bus (USB), etc.

User interface 64, which may be implemented as a control panel or in other manners, allows a user to operate thermal control unit 22. User interface 64 communicates with controller 66 and includes controls 68 enabling a user to turn control unit 22 on and off, select a mode of operation, select a target temperature for the fluid delivered to thermal pads 24, select a patient target temperature, and control other aspects of thermal control unit 22. In some embodiments, user interface may include a pause/event control, a medication control, and/or an automatic temperature adjustment control that operate in accordance with the pause event control 66b, medication control 66c, and automatic temperature adjustment control 66d disclosed in commonly assigned U.S. patent application Ser. No. 62/577,772 filed on Oct. 27, 2017, by inventors Gregory Taylor et al. and entitled THERMAL SYSTEM WITH MEDICATION INTERACTION, the complete disclosure of which is incorporated herein by reference.

In those embodiments where user interface 64 allows a user to select from different modes for controlling the patient's temperature, the different modes include, but are not limited to, a manual mode and an automatic mode, both of which may be used for cooling and heating the patient. In the manual mode, a user selects a target temperature for the fluid that circulates within thermal control unit 22 and that is delivered to thermal pads 24. Control unit 22 then makes adjustments to heat exchanger 40 in order to ensure that the temperature of the fluid exiting supply hoses 26a is at the user-selected temperature.

Another one of the modes is an automatic mode. When the user selects the automatic mode, the user selects a target patient temperature, rather than a target fluid temperature. After selecting the target patient temperature, controller 66 makes automatic adjustments to the temperature of the fluid in order to bring the patient's temperature to the desired patient target temperature. In this mode, the temperature of the circulating fluid may vary as necessary in order to bring about the target patient temperature.

In order to carry out the automatic mode, thermal control unit 22 utilizes patient temperature module 62. Patient temperature module 62 includes one or more patient temperature probe ports 70 (FIGS. 2 & 3) that are adapted to receive one or more conventional patient temperature probes 72. The patient temperature probes 72 may be any suitable patient temperature probe that is able to sense the temperature of the patient at the location of the probe. In one embodiment, the patient temperature probes are conventional Y.S.I. 400 probes marketed by YSI Incorporated of Yellow Springs, Ohio, or probes that are YSI 400 compliant. In other embodiments, different types of probes may be used with thermal control unit 22. Regardless of the specific type of patient temperature probe used in thermal control system 20, each temperature probe 72 is connected to a patient temperature probe port 70 positioned on control unit 22. Patient temperature probe ports 70 are in electrical communication with controller 66 and provide current temperature readings of the patient's temperature.

Figure 4:
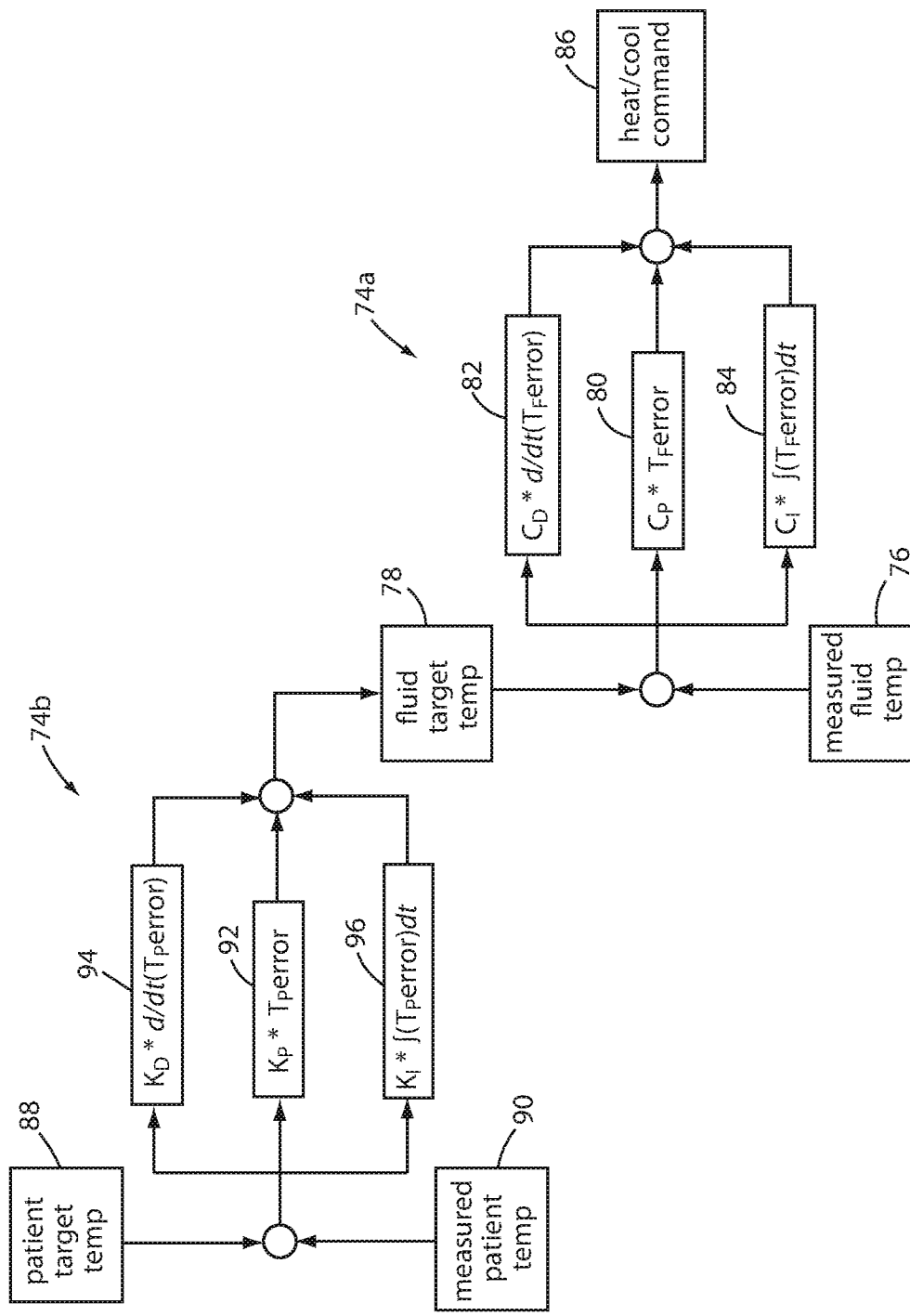
FIG. 4 is an illustrative control loop diagram that may be incorporated into at least one embodiment of the thermal control unit of FIG. 3.

FIG. 4 illustrates a pair of feedback loops 74a and 74b that are used in at least one embodiment of thermal control unit 22. Feedback loop 74a is used by controller 66 when thermal control unit 22 is operating in the manual mode and feedback loops 74a and 74b are both used by controller 66 when thermal control unit 22 is operating in the automatic mode. Feedback loop 74a uses a measured fluid temperature 76 and a fluid target temperature 78 as inputs. Measured fluid temperature 76 comes from outlet temperature sensor 44. Fluid target temperature 78, when thermal control unit 22 is operating in the manual mode, comes from a user inputting a desired fluid temperature using controls 68 of user interface 64. When thermal control unit 22 is operating in the automatic mode, fluid target temperature 78 comes from the output of control loop 74b, as discussed more below.

Control loop 74a determines the difference between the fluid target temperature 78 and the measured fluid temperature 76 ($T_F$error) and uses the resulting error value as an input into a conventional Proportional, Integral, Derivative (PID) control loop. That is, controller 66 multiplies the fluid temperature error by a proportional constant ($C_P$) at step 80, determines the derivative of the fluid temperature error over time and multiplies it by a constant ($C_D$) at step 82, and determines the integral of the fluid temperature error over time and multiplies it by a constant ($C_I$) at step 82. The results of steps 80, 82, and 84 are summed together and converted to a heating/cooling command at step 86. The heating/cooling command is fed to heat exchanger 40 and tells heat exchanger 40 whether to heat and/or cool the circulating fluid and how much heating/cooling power to use.

Control loop 74b which, as noted, is used during the automatic mode, determines the difference between a patient target temperature 88 and a measured patient temperature 90. Patient target temperature 88 is input by a user of thermal control unit 22 using controls 68 of user interface 64. Measured patient temperature 90 comes from a patient temperature probe 72 coupled to one of patient temperature probe ports 70 (FIG. 3). Controller 66 determines the difference between the patient target temperature 88 and the measured patient temperature 90 ($T_P$error) and uses the resulting patient temperature error value as an input into a conventional PID control loop (FIG. 4). As part of the PID loop, controller 66 multiples the patient temperature error by a proportional constant ($K_P$) at step 92, multiplies a derivative of the patient temperature error over time by a derivative constant ($K_D$) at step 94, and multiplies an integral of the patient temperature error over time by an integral constant ($K_I$) at step 96. The results of steps 92, 94, and 96 are summed together and converted to a target fluid temperature value 78. The target fluid temperature value 78 is then fed to control loop 74a, which uses it to compute a fluid temperature error, as discussed above.

It will be understood by those skilled in the art that although FIG. 4 illustrates two PID control loops 74a and 74b, other types of control loops may be used, including, but not limited to, a single control loop or more than two control loops. As other examples, loops 74a and/or 74b can be replaced by one or more PI loops, PD loops, and/or other types of control equations. Controller 66 implements loops 74a and/or 74b multiple times a second in at least one embodiment, although it will be understood that this rate may be varied widely. After controller 66 has output a heat/cool command at step 86 to heat exchanger 40, controller 66 takes another patient temperature reading 90 and/or another fluid temperature reading 76 and re-performs loops 74a and/or 74b. The specific loop(s) used, as noted previously, depends upon whether thermal control unit 22 is operating in the manual mode or automatic mode.

Figure 6:
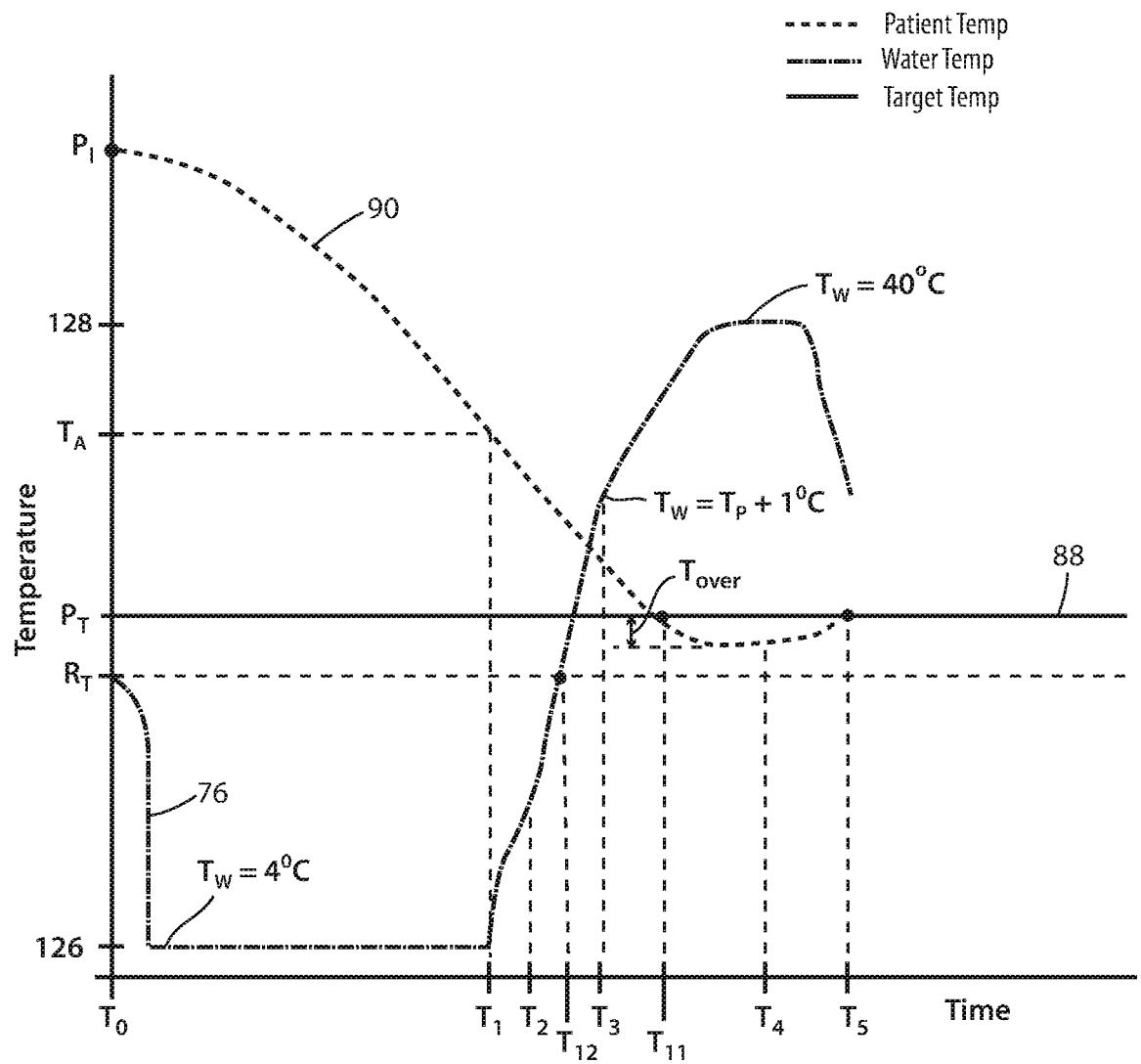
FIG. 6 is a graph of a patient target temperature, patient measured temperature, and fluid temperature illustrating a first example of the temperature control algorithm of FIG. 5.

It will also be understood by those skilled in the art that the output of the control loop 74a may be limited such that the temperature of the fluid delivered to thermal pads 24 by thermal control unit 22 never strays outside of a predefined maximum and a predefined minimum. The predefined minimum temperature, an example of which is shown in FIG. 6 and assigned the reference number 126, is a temperature below which controller 66 does not lower the temperature of the circulating fluid. Minimum temperature 126 is designed as a safety temperature and may vary. In some embodiments, it may be set to about four degrees Celsius, although other temperatures may be selected. The predefined maximum temperature, an example of which is also shown in FIG. 6 and assigned reference number 128, is a temperature above which controller 66 does not heat the circulating fluid. The predetermined maximum temperature 128 is also implemented as a safety measure and may be set to about forty degrees Celsius, although other values may be selected.

Figure 5:
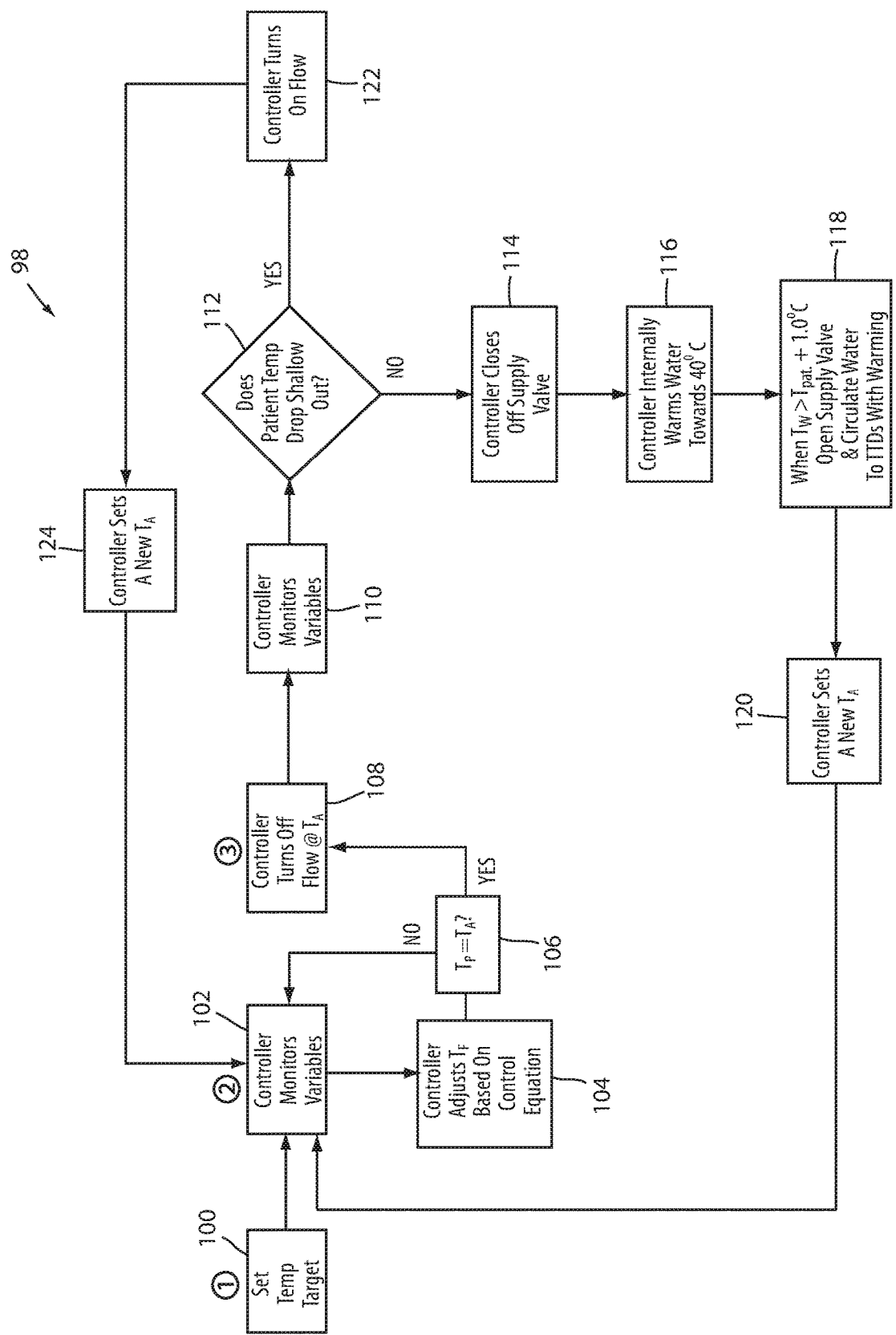
FIG. 5 is a flow diagram of a first temperature control algorithm that may be followed by a controller of the thermal control unit of FIG. 3.

FIG. 5 illustrates in more detail a temperature control algorithm 98 that controller 66 is adapted to implement in some embodiments of thermal control unit 22. Temperature control algorithm 98 is implemented when thermal control unit 22 is operating in the automatic mode—that is, when thermal control unit 22 is heating and/or cooling the temperature of the circulating fluid in order to automatically bring the temperature of the patient to a target temperature, and/or to maintain the patient temperature at the selected target temperature. Algorithm 98 begins at a temperature selection step 100 in which a user selects the patient target temperature 88.

After selecting the patient target temperature 88, controller 66 moves to step 102 where it takes readings of the basic variables used in controlling the patient's temperature. These basic variables include the fluid temperature (measured by outlet temperature sensor 44), the patient temperature 90 (as measured by a patient temperature probe 72), and the patient target temperature 88 (as input by a user). In alternative embodiments, one or more additional readings may be taken, such as one or more measurements of the flow rate of fluid in circulation channel 36, a pump speed, a temperature of fluid returning into inlet manifold 50, the amount of heat removed from, or added to, the patient, and/or other variables.

After taking readings of the basic variables at step 102, controller 66 moves to step 104 where it implements the computations of control loops 74a and 74b (FIG. 4). That is, controller 66 determines the current error between the patient's measured temperature 90 and the patient target temperature 88 and feeds these variables into control loop 74b (FIG. 4). The output of control loop 74b is a target fluid temperature 78, which controller compares against the current fluid temperature 76 to determine a fluid temperature error for use in control loop 74a. After determining the fluid temperature error, controller 66 performs steps 80-84 and outputs a heating/cooling command at step 86 to heat exchanger 40.

After control loops 74a and 74b have been completed once (or more than once), controller 66 moves onto step 106 (FIG. 5). At step 106 controller 66 determines whether a current patient temperature reading ($T_P$) taken from patient temperature probe 72 is equal to a threshold temperature $T_A$. If the current patient temperature is not yet equal to the temperature threshold $T_A$, controller 66 returns to step 102 where it takes fresh readings of the patient temperature 90 and fluid temperature 76 for use in repeating step 104 in the manner described. If the current patient temperature is equal to the temperature threshold $T_A$ at step 106, controller 66 moves onto step 108, as will be discussed more below.

The temperature threshold $T_A$ used in step 106 is a temperature that is intermediate the initial temperature of the patient ($P_I$; FIG. 6) when algorithm 98 starts and the patient target temperature 88. In some embodiments, $T_A$ is based on a specific patient temperature value, such as, but not limited to a patient temperature value that is approximately half way between the patient's initial temperature ($P_I$) and the patient's target temperature 88. Thus, for example, if the patient's initial temperature is thirty-seven degrees Celsius and the target patient temperature is thirty-three degrees Celsius, $T_A$ may be set equal to thirty-five degrees Celsius. In some embodiments, $T_A$ is not a temperature magnitude, but a slope magnitude that has to be met by the slope of recent patient temperature readings 90 before controller 66 moves onto step 108. In still other embodiments, $T_A$ is based on a combination of the slope of the patient temperature readings and also a specific patient temperature value. In these latter embodiments, controller 66 may look for a specific threshold slope to be achieved before then examining whether a specific temperature is achieved, or vice versa. Still other ways of combining a value and the rate of change of that value may be used.

If controller 66 determines at step 106 (FIG. 5) that the patient's current temperature is equal to $T_A$ or has moved past $T_A$, controller 66 moves to step 108. At step 108, controller 66 stops the flow of fluid to the thermal pads 24. Controller 66 may achieve this termination of fluid flow in different manners. In one embodiment, controller 66 closes bypass valve 56 such that the fluid being pumped by pump 34 is diverted to bypass line 52 and does not exit out of outlet ports 46. In an alternative embodiment, controller 66 stops the fluid flow to thermal pads 24 by switching off pump 34. In either embodiment, controller 66 thereafter proceeds to step 110 and monitors the patient temperature while the fluid flow to pads 24 has been temporarily terminated.

At step 110 (FIG. 5), controller 66 determines how the patient's temperature readings 90 react to the cessation of fluid to thermal pads 24. Controller 66 determines this reaction over a predefined amount of time, which may be on the order of several minutes or more, although a variety of different time periods may be used. Controller 66 specifically measures and monitors changes in the slope of the patient temperature readings 90 at step 110 while the flow of fluid is terminated to pads 24. Controller 66 monitors changes in the slope of the patient temperature readings 90 in order to assess whether the patient's temperature will likely reach the patient target temperature 88 within a desired time period without further fluid being supplied to thermal pads 24, or whether it is unlikely that the patient's temperature will reach the patient target temperature 88 within the desired time period without supplying additional fluid to thermal pads 24. This assessment occurs at step 112, and the desired time period may be set based upon the absolute value of $T_A$, the difference between the patient's current temperature and target temperature, and/or other factors.

At step 112, controller 66 determines whether the slope of the patient temperature readings shallows out or not within the time period during which the fluid flow is ceased. This assessment is based upon whether or not the change in the slope of the temperature exceeds one or more thresholds. FIGS. 6 and 7 provide two examples of this assessment. In FIG. 6, the patient is being cooled from an initial patient temperature $P_I$ toward a target temperature PT. As shown therein, the patient's temperature reaches point $T_A$ at time $T_1$. Controller 66 therefore turns off fluid flow to the thermal pads 24 at time $T_1$ in accordance with step 108 of algorithm 98 (FIG. 5). From time $T_1$ to time $T_2$, controller 66 monitors the change in the patient's temperature 90 and determines whether the change in this temperature has shallowed out more than a threshold or not, in accordance with steps 110 and 112 of algorithm 98.

In the particular example of FIG. 6, it can be seen that the slope of the patient temperature readings 90 has changed very little in the interim between times $T_1$ and $T_2$ when compared with the slope of the patient temperature readings 90 in the moments before $T_1$. That is, the rate at which the patient's temperature was dropping in the moments prior to time $T_1$ did not change much in the interim time period between times $T_1$ and $T_2$. Accordingly, it is likely that the patient's temperature will continue to drop sufficiently far to reach the target temperature 88 without further fluid being delivered to thermal pads 24. Accordingly, controller 66 moves from step 112 to step 114.

At step 114 (FIG. 5), controller 66 closes bypass valve 56 (to the extent it wasn't already closed at step 108). Controller 66 then moves onto step 116 where it begins warming the circulating fluid towards a higher temperature (such as, but not limited to, maximum temperature 128, a temperature that is a predetermined amount above the patient's target temperature, or another temperature). Controller 66 carries out the warming at step 116 by starting pump 34 (if it was previously stopped at step 108), or continuing to run pump 34 (if it was not previously stopped at step 108) and sending heating instructions to heat exchanger 40. During this time, because bypass valve 56 remains closed, the fluid inside of thermal control unit 22 circulates purely internally within thermal control unit 22 and circulation channel 36. Because circulation channel 36 passes through heat exchanger 40, this internal circulation heats the fluid as it passes through heat exchanger 40.

The heating of fluid within thermal control unit 22 carried out during step 116 (FIG. 5) continues until time $T_3$ is reached (FIG. 6). Time $T_3$ is the time at which the fluid temperature 76 meets or exceeds the current patient temperature 90 and it corresponds to the time at which step 118 is carried out in FIG. 5. In the example illustrated in FIG. 6, time $T_3$ is the time at which the fluid temperature 76 exceeds the patient temperature 90 by one degree Celsius. At time $T_3$, controller 66 opens bypass valve 56 so that the circulating fluid is able to flow to outlet manifold 42, which in turn delivers the fluid to thermal pads 24. Accordingly, at time $T_3$, the warmed fluid is delivered to the patient.

This warmed fluid is delivered to the patient at time $T_3$ in order to prevent overshoot of the patient's temperature. In the specific example of FIG. 6, the warmed fluid is delivered to the patient slightly prior to the patient's temperature reaching the target temperature 88. In the absence of the delivery of the warmed fluid, the patient's temperature would likely continue downward and past the target temperature to a greater extent than the overshoot illustrated (rover). Accordingly, by delivering the warmed fluid to thermal pads 24 prior to reaching the target temperature, the rate of the patient's temperature drop can be slowed to close to zero at or near the moment the patient reaches the target temperature. In this manner, the patient's target temperature is reached more quickly, but with reduced overshoot.

During the warming of the fluid between time $T_2$ and $T_3$, controller 66 may take and analyze additional readings of the patient's temperature to see if the patient's temperature is continuing to move toward the target temperature 88. In the event the patient's progress toward target temperature 88 stalls or stops, controller 66 may be programmed to carry out step 118 (open bypass valve 56) sooner or later than it otherwise would (depending on the current temperature of the fluid in thermal control unit 22) if supplying the fluid at its current temperature to the thermal pads 24 would help advance the patient's progress toward target temperature 88. Controller 66 may therefore determine time $T_3$ in some embodiments by calculating the difference between the patient's temperature 90 and the target temperature 88 and/or by calculating the slope of the patient's temperature 90. These calculations may be done either in lieu of or in addition to the aforementioned comparison of the fluid temperature to the patient's temperature. In other words, $T_3$ may be defined strictly on a comparison between the current fluid temperature and patient temperature, or it may be defined based on the slope of the patient's temperature, or it may be defined on the distance between the patient's temperature 90 and the target temperature 88, or a combination of any of these.

As a result, if the patient is taking longer to reach target temperature 88 than was anticipated by controller 66 at time $T_1$, controller 66 may delay the delivery of warm fluid to the thermal pads past the moment the fluid temperature is equal to, or more than one degree Celsius above, the patient's temperature. In this manner, the delivery of the warm fluid is delayed so that it doesn't cause the patient's temperature to possibly not reach the target temperature 88. Alternatively, or additionally, controller 66 may expedite the delivery of warm fluid to the thermal pads 24 prior to the moment the fluid temperature is equal to, or more than one degree above, the patient's temperature. Such expediting is performed if the patient's temperature drops faster than controller 66 had anticipated at time $T_1$.

With respect to FIG. 6, controller 66 uses the control loops 74a and 74b to control the temperature of the circulating fluid between the beginning of thermal therapy (time $T_0$) and time $T_1$. Between time $T_1$ and $T_2$, controller 66 may deactivate the heat exchanger, or it may continue to control the temperature of the fluid using control loops 74a and 74b, or it may control the heat exchanger 40 in another matter. Different embodiments may select different ones of these options. The different options are available because during the time period from $T_1$ to $T_2$, fluid is not being delivered to the patient, so the precise manner in which the fluid temperature is controlled is not critical. In the time period between $T_2$ and $T_3$, controller 66 may use control loop 74a (with the target fluid temperature set to a maximum or to a predetermined amount above the patient target temperature 88) to heat the fluid, or it may use open loop heating. After time $T_3$, controller 66 switches back to using control loops 74a and 74b (to the extent it hasn't switched back earlier).

One of the reasons why controller 66 stops delivering temperature-controlled fluid to the thermal pads 24 at time $T_2$ is because the temperature reaction of patients to the thermal treatment varies from individual patient to individual patient. It can therefore be difficult to tune a PID (or other type) of control loop to change an individual patient's temperature in the most efficient manner without overshoot. By stopping the delivery of fluid to the patient, however, controller 66 is able to assess the individual temperature response of the particular patient undergoing thermal treatment at that time. This individual assessment allows for control of the temperature of the circulating fluid that is more specifically tailored to the individual undergoing thermal treatment. Without this individually tailored control, the PID control loops 74a and 74b (or other types of control loops) may not start warming patient until the patient temperature reaches target temperature 88, or only a short time period before then. In either case, due to the amount of time it takes to warm the fluid, fluid will likely be delivered to the patient that is below the target temperature 88 after the patient has already reached target temperature 88, which will likely further exacerbate the overshoot.

Returning to FIG. 5, after controller 66 opens bypass valve 56 at step 118, controller 66 moves to step 120 and calculates a new time $T_A$ at step 122. The calculation of a new time $T_A$ at step 120 is an optional step. In some embodiments, algorithm 98 includes step 120, while in other embodiments, algorithm 98 does not include step 120. When algorithm 98 does not include step 120, controller 66 returns to controlling the temperature of the fluid using control loops 74a and 74b for the remainder of the thermal treatment session. When algorithm 98 does include step 120, controller 66 calculates a new $T_A$ value in order to help future overshoot on the opposite side of the patient's target temperature 88. In other words, the repetition of steps 100-118 via step 120 is designed to reduce overshoot after the patient's temperature reaches the target temperature the second time (or a third time, a fourth time, etc.). In the example of FIG. 6, step 120 helps reduce any overshoot that occurs after time $T_5$.

The value of the new $T_A$ set at step 120 may be determined in multiple manners. In some embodiments, the value is set to be less than the patient target temperature 88 by a fraction of the overshoot value $T_{over}$ (FIG. 6). The fraction may be one-half in some embodiments, although other fractions may be used. In still other embodiments, $T_A$ may be defined in another manner.

In the illustrative graph shown in FIG. 6, controller 66 has not implemented step 120. However, the following description of step 120 will utilize the graph of FIG. 6 to more fully explain the overshoot reduction accomplished via step 120. After calculating a new $T_A$ at step 120, controller 66 returns to steps 102, 104, and 106, where it monitors the patient temperature and the fluid temperature (step 102), controls the fluid temperature using control loops 74a and 74b (step 104), and compares the patient temperature to the new $T_A$ value (calculated in step 120). Thus, controller 66 implements the loop of steps 102, 104, and 106 until the patient's temperature reaches the new $T_A$ value. Although controller 66 has not utilized step 120 in FIG. 6 (as noted above), FIG. 6 includes a time labeled $T_4$, and $T_4$ corresponds to one potential time at which the patient's temperature would equal the new $T_A$ value were controller 66 implementing step 120.

At time $T_4$, controller 66 would move onto step 108 and stop the flow of fluid, and thereafter follow steps 110-118 in the manner previously described. These steps would help reduce the second overshoot of the patient's temperature past target temperature 88. It can be seen from FIG. 6, however, that step 120 was not actually performed in the example illustrated therein because, when the patient reaches the target temperature 88 for the second time at $T_5$, the fluid temperature 76 is well above the target temperature 88. Consequently, the continued delivery of fluid at this elevated temperature to the thermal pads 24 would likely cause the patient's temperature to rise above (overshoot) the target temperature 88 in the time period subsequent to time $T_5$. Had step 120 been performed in the example of FIG. 6, controller 66 would have begun reducing the temperature of the fluid at a point earlier than shown in FIG. 6 so that, at point $T_5$, the temperature of the fluid 76 was significantly closer to the target temperature 88.

Returning to step 112 of algorithm 98 (FIG. 5), controller 66 proceeds to step 122 (and does not shut off bypass valve 56) if it detects that the rate of change of the patient's temperature has started to shallow out by more than the threshold used in step 112. FIG. 7 illustrates an example of this situation. Time $T_6$ of FIG. 7 corresponds to step 108 in algorithm 98. That is, controller 66 has determined at time $T_6$ of FIG. 7 that the patient's temperature has reached temperature $T_4$. Controller 66 therefore shuts off bypass valve 56 at time $T_6$ and begins monitoring the reaction of the patient's temperature to this shut off. This monitoring takes place from time $T_6$ to $T_7$ and is performed in step 110. As can be seen in FIG. 7, in the moments after $T_6$ (and before $T_7$), the rate at which the patient's temperature 90 is dropping changes significantly from the rate at which the patient's temperature 90 dropped in the moments before $T_6$. Controller 66 therefore determines that the patient is unlikely to reach the target temperature 88 without supplying additional cold fluid to thermal pads 24. In other words, controller 66 determines at step 112 that the patient's rate of temperature change has shallowed out more than a threshold, and therefore proceeds to step 122.

At step 122, controller 66 opens up bypass valve 56, restarting the supply of cold fluid to thermal pads 24. Controller 66 also restarts (to the extent it had stopped doing so at time $T_6$) the temperature control of the circulating fluid using control loops 74a and 74b. In the example shown in FIG. 7, controller 66 starts warming the fluid inside thermal control unit 22 in the time period between $T_6$ and $T_7$, and controller 66 terminates this warming at time $T_7$ (and starts using control loops 74a and 74b again). In other embodiments, controller 66 may simply shut off heat exchanger 40 in the interim between $T_6$ and $T_7$.

After opening bypass valve 56 at step 122, controller 66 proceeds to step 124 where it calculates a new $T_A$ value. The new $T_A$ value of step 124 is not the same as the new $T_A$ value calculated in step 120, although it may be calculated in a number of different manners. In one embodiment, the new $T_A$ value of step 124 is set equal to a value halfway between the patient target temperature 88 and the old $T_A$ value (e.g. $T_A$new=$((T_A$old−Pat. Targ. Temp)/2)+Pat. Targ. Temp.) Variations of this formula, or still other manners of calculating the new $T_A$ value at step 124, may be used. After calculating the new $T_A$ value, controller 66 proceeds back to step 102 where it recommences reading the fluid and patient temperatures. After reading the fluid and patient temperatures at step 102, the fluid and patient temperature values are used in the control loops 74a and 74b at step 104. Control then moves to step 106 where controller 66 determines whether the patient's temperature has reached the new $T_A$ value that was calculated at step 124. Steps 102, 104, and 106 continue until the patient's temperature reaches the new $T_A$ value. This point is labeled $T_8$ in FIG. 7 and corresponds to step 108.

At step 108, controller 66 shuts off bypass valve 56 again and proceeds to repeat steps 110 and 112 in the same manner previously described. With respect to FIG. 7, controller 66 closes the bypass valve at $T_8$, monitors the temperature variables at step 110 until time $T_9$, and then proceeds to step 112. In the example of FIG. 7, controller 66 determines at step 112 (time $T_9$) that the rate of change of the patient's temperature between times $T_8$ and $T_9$ has not bottomed out so much that the patient will not likely reach target temperature 88 without further fluid delivery to thermal pads 24. In other words, at time $T_9$, controller 66 moves to step 114 and shuts off bypass valve 56. Controller 66 leaves bypass valve 56 shut off until time $T_{10}$, at which point the fluid has warmed sufficiently to help prevent overshoot of the patient's temperature. Accordingly, at time $T_{10}$ (step 118) controller 66 opens bypass valve 56 again and begins delivering fluid to thermal pads 24.

In the example illustrated in FIG. 6, algorithm 98 reaches step 112 once and proceeds to step 114. In the example illustrated in FIG. 7, algorithm 98 reaches step 112 twice and the first time controller 66 proceeds to step 122 and second time controller 66 proceeds to step 114. It will be understood, of course, that FIGS. 6 and 7 illustrate only two potential usage scenarios of algorithm 98, and that many other variations are possible. For example, there is no limit to the number of times controller 66 might proceed to step 122 before eventually proceeding to step 114. As another example, neither FIG. 6 nor FIG. 7 illustrates a situation where step 120 is followed. In those situations where controller 66 executes step 120, controller 66 may subsequently branch to step 122 at step 112 or it may branch to step 114 at step 112. After moving through steps 114, 116, and 118 a second time, controller 66 may be programmed to proceed to step 120 yet another time.

Although algorithm 98 has been described herein as stopping the flow of fluid to thermal pads 24 at step 108, it will be understood that various modifications can be made to this. In one modified embodiment, controller 66 deactivates heat exchanger 40 but continues to supply fluid to thermal pads 24 at step 108 and reactivates heat exchanger 40 at steps 116 and/or 122 (and continues to supply fluid to thermal pads 24). The remainder of algorithm 98 remains the same in this modified embodiment. In other modified embodiments, controller 66 reduces the flow of fluid to thermal pads 24 at step 108, but does not completely stop the flow of fluid. Full fluid delivery to pads 24 returns at steps 116 and/or 122. In still other modified embodiments, controller 66 combines the reduction of fluid flow at step 108 with the deactivation of heat exchanger 40, and the resumption of full fluid flow at steps 116 and 122 with the reactivation of heat exchanger 40. Still other variations are possible.

It will be understood that, although FIGS. 6 and 7 illustrate algorithm 98 being applied to a situation where the patient's target temperature 88 is set below the patient's initial temperature (i.e. the patient is being cooled by thermal control system 20), algorithm 98 is equally applicable to situations in which the patient is being warmed. Indeed, algorithm 98 is agnostic as to relationship of the patient's initial temperature to the target temperature 88. The same steps and calculations as discussed above with respect to FIGS. 5-7 are used regardless of whether thermal control system 20 is being used to cool or warm a patient.

Figure 8:
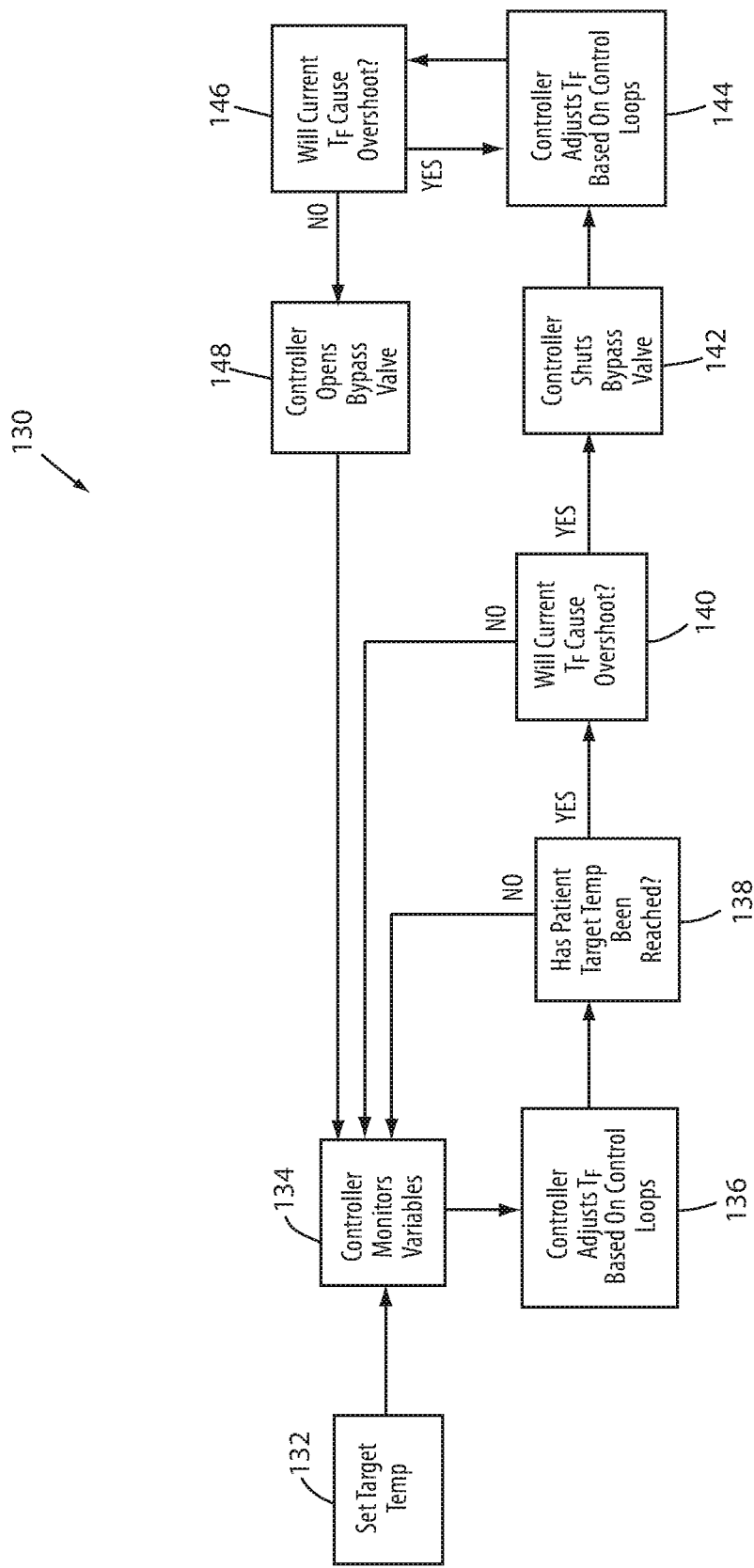
FIG. 8 is a flow diagram of a second temperature control algorithm that may be followed by a controller of the thermal control unit of FIG. 3.

FIG. 8 illustrates a second temperature control algorithm 130 that may be followed by controller 66 of thermal control unit 22. Control algorithm 130 begins at step 132 where a user sets a desired patient target temperature 88. Step 132 is the same as step 100 of algorithm 98. After step 132, controller 66 proceeds to step 134 where it takes readings of the patient's temperature, the fluid temperature inside thermal control unit 22, and determines the slope and/or other characteristics of past values of these temperatures. Step 134 is also the same as step 102 of algorithm 98.

After step 134, controller 66 moves to step 136 where it uses the latest readings of the patient's temperature 90 and the fluid temperature 76 in the control loops 74a and 74b. Controller 66 then sends a heating/cooling command to heat exchanger 40 based on the output of these control loops. Step 136 is the same as step 104 of algorithm 98.

After step 136, controller 66 moves to step 138 where it determines whether or not the patient has yet reached the target temperature 88. If the patient has not yet reached target temperature 88, control returns to steps 134 and 136 and controller 66 continues to send heating and cooling commands to heat exchanger 40 using the closed control loops 74a and 74b and the current readings of patient and fluid temperature taken during steps 134.

When the patient's temperature 90 eventually reaches the target temperature, controller 66 moves from step 138 to step 140. At step 140, controller 66 determines whether the current temperature of the fluid 76 will cause or exacerbate overshoot of the target temperature 88 if the fluid is delivered to thermal pads 24. This is determined by examining the current fluid temperature 76 and determining whether the patient's arrival at the target temperature occurred through cooling or through heating. If the patient arrived at the target temperature 88 by cooling, controller 66 determines at step 140 if the current temperature of the fluid is less than target temperature 88. If it is, controller 66 concludes that continuing to deliver fluid to thermal pads 24 at a temperature below target temperature 88 to a patient who was just cooled to target temperature 88 will likely cause or exacerbate overshoot, and controller 66 therefore moves to step 142 where it shuts off bypass valve 56. If it is not, controller 66 concludes that continuing to deliver fluid to thermal pads 24 at a temperature warmer than the target temperature will likely not cause or exacerbate overshoot, and therefore moves back to step 134 while keeping bypass valve 56 open.

Conversely, if the patient arrived at target temperature 88 by warming, controller 66 determines at step 140 if the current temperature of the fluid is more than target temperature 88. If it is, controller 66 concludes that continuing to deliver fluid to thermal pads 24 at a temperature above target temperature 88 to a patient who was just warmed to target temperature 88 will likely cause or exacerbate overshoot, and controller 66 therefore moves to step 142 where it shuts off bypass valve 56. If it is not, controller 66 concludes that continuing to deliver fluid to thermal pads 24 at a temperature below target temperature 88 will not likely cause or exacerbate overshoot, and therefore moves back to step 134 while keeping bypass valve 56 open.

The determinations made by controller 66 at step 140 may be better understood with respect to the example shown in FIG. 6. Although FIG. 6 illustrates an example of patient and fluid temperatures when thermal control unit 22 is following algorithm 98, the graphs of temperature shown therein can be used to explain when and how controller 66 makes its decision at step 140. The results of those decisions, however, are not shown in FIG. 6 because, as noted, FIG. 6 illustrates an exemplary result of control algorithm 98, not control algorithm 130.

The decision of step 140 of algorithm 130 is first made when the patient's temperature reaches the target temperature 88 for the first time, which in the graph of FIG. 6 occurs at time $T_{11}$. Further, in the graph of FIG. 6, the patient arrives at target temperature 88 at time $T_{11}$ after being cooled. Accordingly, at time $T_{11}$, controller 66—when following algorithm 130—looks at the temperature of the fluid 76 at time $T_{11}$. In FIG. 6, this fluid temperature 76 is above target temperature 88. Consequently, if controller 66 continues to deliver this fluid to thermal pads 24, it is not going to cause or exacerbate overshoot. Instead, it will resist overshoot. This is because any overshoot that occurs at time $T_{11}$ will be an overshoot where the patient's temperature moves below target temperature 88. As a result, by delivering fluid to thermal pads 24 that is warmer than target temperature 88, the patient's overshoot will be reduced (or eliminated). Had the fluid temperature 76 in FIG. 6 been below target temperature 88 at time $T_{11}$, controller 66 would have concluded that continued delivery of the fluid to thermal pads 24 at time $T_{11}$ would exacerbate the overshoot, and therefore would have moved to step 142 of algorithm 130 and shut off bypass valve 56.

FIG. 6 also illustrates the patient's temperature arriving at target temperature 88 a second time. This occurs at time $T_5$. When controller 66 is following algorithm 130 and the patient arrives at the target temperature 88 for the second time (or any times thereafter), controller 66 once again goes through the above-described analysis at step 140. In the example shown in FIG. 6, controller 66 would proceed to step 142 and shut off bypass valve 56 at time $T_5$. This is because the patient arrived at target temperature 88 at time $T_5$ by being warmed and the temperature of the fluid 76 at time $T_5$ is above target temperature 88. Accordingly, if thermal control unit 22 were to continue to deliver fluid to thermal pads 24 at time $T_5$ (and thereafter), the fluid would continue to warm the patient, which would lead to greater overshoot. Accordingly, in the example shown in FIG. 6, controller 66 would move to step 142 of algorithm 130 and shut off bypass valve 56.

After controller 66 has moved to step 142, it follows steps 144 and 146 to determine when to open up bypass valve 56. At step 144, controller 66 continues to heat or cool the circulating fluid in accordance with the commands generated from control loops 74a and 74b. At step 146, controller 66 performs the same analysis it did at step 140. That is, it looks at the current patient temperature and the current fluid temperature and determines whether or not the delivery of fluid at its current temperature to thermal pads 24 would cause or exacerbate overshoot. If it would, control returns back to step 144 where further temperature adjustments are made. After the further temperature adjustments are made, controller 66 moves again to step 146 to determine if overshoot will occur or be exacerbated by delivering the fluid to the thermal pads. This back and forth between steps 144 and 146 keeps on going until the fluid eventually reaches a temperature where it will not cause or exacerbate any overshoot in the patient's temperature. At that point, controller 66 moves to step 148 where it opens bypass valve 56, allowing fluid to flow again to thermal pads 24. After step 148, controller 66 returns to step 134.

During the performance of steps 144 and 146, which may continue for as long as necessary for thermal control unit 22 to adjust the fluid temperature to a point where its delivery to thermal pads 24 will not cause or exacerbate overshoot, bypass valve 56 remains closed. As a result, the heating or cooling of the fluid that occurs during these steps is confined to thermal control unit 22. Pump 34 remains active during this time, but the circulation caused by pump 34 is restricted to occurring only internally because all of the fluid travels through bypass line 52 rather than exiting out outlet manifold 42.

In the example of algorithm 130 described above, the determination of whether or not fluid delivery to thermal pads will contribute to overshoot is based on examining the current fluid temperature's relationship to the target temperature 88. It will be understood that this examination may be modified. In some embodiments, for example, controller 66 examines the current fluid temperature's relationship to a different value, such as range of temperatures (which may be defined with respect to the target temperature). In some such embodiments, whether or not the current fluid temperature 76 falls within that range or not is the sole criteria for determining whether to open or close bypass valve 56 at steps 142 and 148. In other of such embodiments, whether or not the current fluid temperature 76 falls within that range or not is used in conjunction with other factors to determine whether to open or close bypass valve 56. The other factors include, but are not limited to, the determination of whether the patient's temperature 90 arrived at target temperature 88 via heating or cooling, as noted above.

Figure 9:
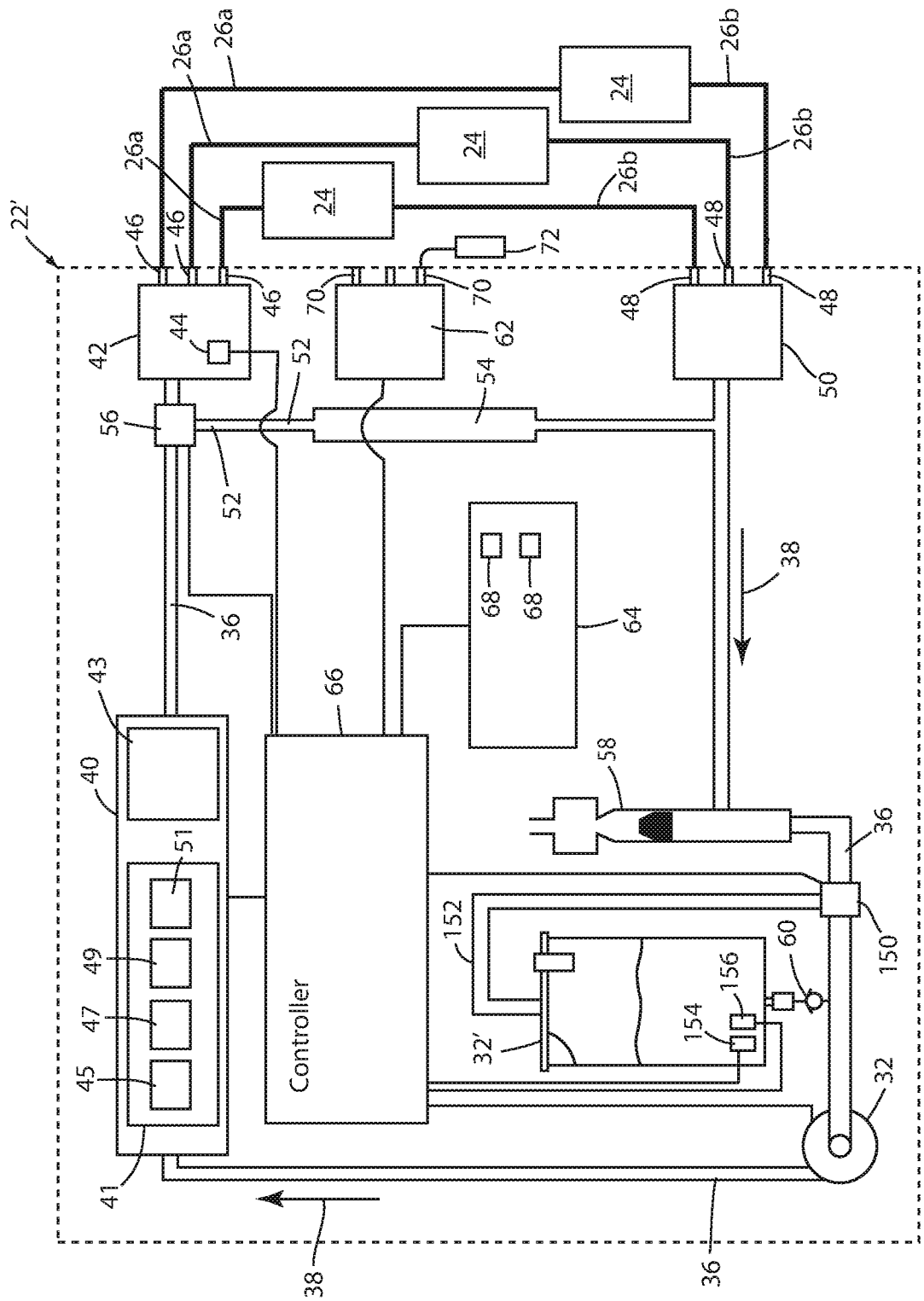
FIG. 9 is a block diagram of a second embodiment of the thermal control unit of FIG. 2.

FIG. 9 illustrates an alternative embodiment of a thermal control unit 22'. Those elements of thermal control unit 22' that are the same as thermal control unit 22 are labeled with the same reference number and, unless explicitly mentioned otherwise below, operate in the same manner as described with respect to thermal control unit 22. Those elements of thermal control unit 22' that are new are provided with a new reference number, and those elements of thermal control unit 22' that are similar but modified from thermal control unit 22 are provided with the same reference number followed by a prime (') symbol. Thermal control unit 22' of FIG. 9 differs from thermal control unit 22 in that thermal control unit 22' is adapted to selectively move fluid reservoir 32' into and out of line with circulation channel 36. Thermal control unit 22' accomplishes this through the inclusion of reservoir valve 150. Reservoir valve 150 is shown positioned in FIG. 9 in circulation channel 36 between air remover 58 and valve 60, although it will be understood that reservoir valve 150 may be moved to different locations within circulation channel 36. Reservoir valve 150 is coupled to circulation channel 36 as well as a reservoir channel 152.

When reservoir valve 150 is open, fluid from air remover 58 flows along circulation channel 36 to pump 34 without passing through reservoir 32' and without any fluid flowing along reservoir channel 152. When reservoir valve 150 is closed, fluid from air remover 58 flows along reservoir channel 152, which feeds the fluid into reservoir 32'. Fluid inside of reservoir 32' then flows back into circulation channel 36 via valve 60. Once back in circulation channel 36, the fluid flows to pump 34 and is pumped to the rest of circulation channel 36 and thermal pads 24 and/or bypass line 52. In some embodiments, reservoir valve 150 is controllable to be either fully open or fully closed, while in other embodiments, reservoir valve 150 is controllable to be partially open or partially closed. In either case, reservoir valve 150 is under the control of controller 66. Controller 66 opens and closes reservoir valve 150 in some embodiments when disinfectant is mixed into the circulating fluid in order to disinfect reservoir 32' and circulation channel 36. Controller 66 also closes and opens reservoir valve 150 for other purposes which are discussed in greater detail below.

Thermal control unit 22' also includes a reservoir temperature sensor 154. Reservoir temperature sensor 154 reports its temperature readings to controller 66. When reservoir valve 150 is open, the fluid inside of reservoir 32' stays inside of reservoir 32' (after the initial drainage of the amount of fluid needed to fill circulation channel 36 and thermal pads 24). This residual fluid is not affected by the temperature changes made to the fluid within circulation channel 36 as long as reservoir valve 150 remains open. This is because the residual fluid that remains inside of reservoir 32' after circulation channel 36 and thermal pads 24 have been filled does not pass through heat exchanger 40 and remains substantially thermally isolated from the circulating fluid. Two results flow from this: first, heat exchanger 40 does not need to expend energy on changing the temperature of the residual fluid in reservoir 32', and second, the temperature of the circulating fluid in circulation channel 36 will deviate from the temperature of the residual fluid as the circulating fluid circulates through heat exchanger 40.

Figure 10:
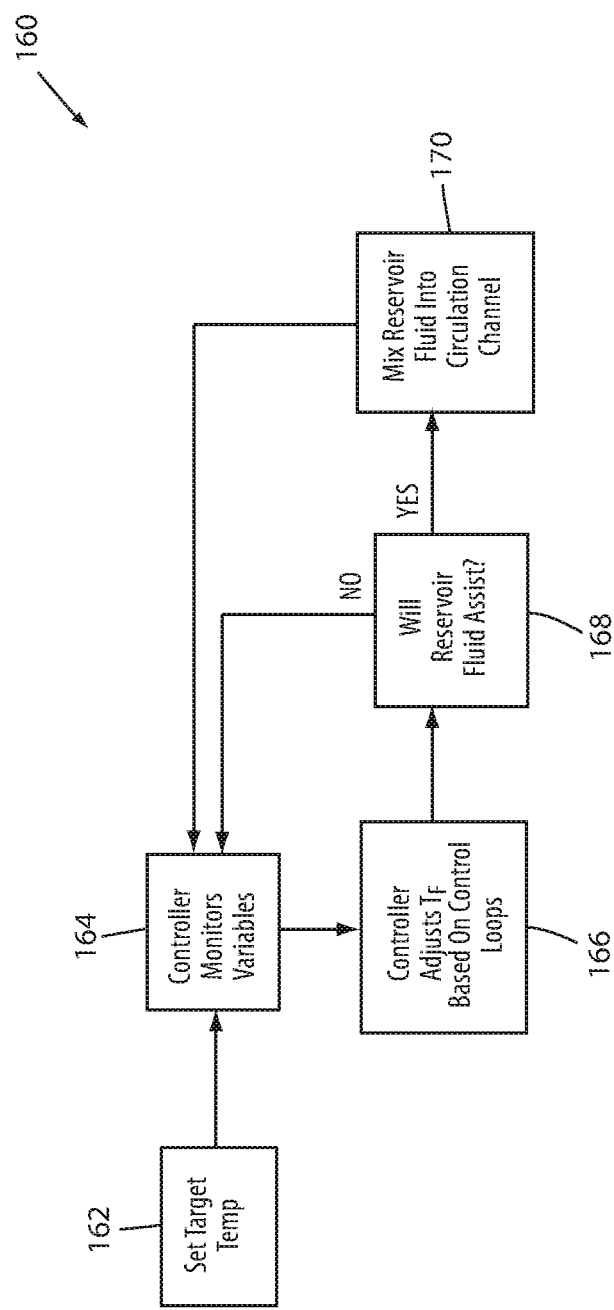
FIG. 10 is a flow diagram of a third temperature control algorithm that may be followed by a controller of the thermal control unit of FIG. 9.

Temperature control algorithm 160 of FIG. 10 utilizes the divergence between the temperature of the residual fluid in reservoir 32' and the temperature of the circulating fluid when it is advantageous to do so. That is, controller 66 monitors the temperature of the residual fluid in reservoir 32' and if it warmer than the circulating fluid in circulation channel 36, controller 66 may selectively close valve 150 and mix some or all of the residual fluid into circulation channel 36 if controller 66 needs to quickly warm the temperature of the circulating fluid. Similarly, if the temperature of the residual fluid is colder than the temperature of the circulating fluid, controller 66 may selective close valve 150 and mix some or all of the residual fluid into circulation channel 36 if controller 66 needs to quickly cool the temperature of the circulating fluid. The details of control algorithm 160 will now be described with respect to FIG. 10.

Control algorithm 160 starts at step 162 where the user selects a target temperature 88 for the patient. From step 162, controller 66 moves to step 164 where it takes fluid temperature and patient temperature readings. The readings are used by controller 66 during step 166 to determine what heating or cooling command to issue to heat exchanger 40. The command to issue to heat exchanger 40 is determined at step 166 using control loops 74a and 74b. After sending out one or more heating or cooling commands at step 166, controller 66 moves to step 168 where it determines whether or not the addition of the residual fluid inside reservoir 32' would be helpful in achieving a target temperature for the circulating fluid. This determination is made using a current reading of the temperature of the residual fluid inside reservoir 32' (as measured by sensor 154), a current reading of the circulating fluid inside thermal control unit 22' (as measured by outlet temp sensor 44), and the patient target temperature 88.

In general, controller 66 does not initially utilize any of the residual fluid inside reservoir 32' until after the patient has reached target temperature 88 the first time (e.g. time $T_{11}$ in FIG. 6 or shortly after time $T_{10}$ in FIG. 7). This is because when thermal control unit 22' is initially used, the residual fluid tends to remain at room temperature while the circulating fluid is controlled via heat exchanger 40 toward a temperature that will either heat or cool the patient to the target temperature. During that initial heating or cooling of the patient, the residual fluid at room temperature will not be helpful. However, once the patient has reached the target temperature 88 (or once the patient has come close to the target temperature 88, such as, but not limited to, temperature $T_A$ discussed above with respect to algorithm 98), controller 66 generally needs to switch from heating the circulating fluid to cooling the circulating fluid, or vice versa. It is at these changes in thermal direction that the residual fluid inside of reservoir 32' can be most helpful for rapidly changing the temperature of the circulating fluid. It will be understood, however, that controller 66 may utilize the residual fluid inside of reservoir 32' at other times, including before the patient reaches the target temperature.

Controller determines whether the residual fluid is helpful or not at these moments by determining if the temperature of the residual fluid is closer to the fluid target temperature 78 than the current temperature of the circulating fluid. If it is, controller 66 moves to step 170 and closes reservoir valve 150 such that the reservoir 32' becomes part of circulation channel 36. That is, instead of diverting the circulating fluid around reservoir 32' (which occurs when valve 150 is open), the closing of valve 150 diverts the circulating fluid through reservoir 32'. The residual fluid is thus mixed with the circulating fluid and the temperature of the circulating fluid is quickly adjusted upward or downward, depending upon the difference in temperature between the circulating fluid and the residual fluid.

In some embodiments, controller 66 keeps valve 150 closed for as long as it takes to ensure that all, or substantially all, of the residual fluid inside reservoir 32' has passed out of reservoir 32' and mixed into the fluid inside of circulating channel 36. In order to measure this amount of time, thermal control unit 22' may include a depth or volume sensor to measure how much residual fluid is in reservoir 32', as well as one or more flow sensors that measure how much fluid has been delivered to fluid reservoir 32' from reservoir channel 152. In other embodiments, controller 66 may continue to close valve 150 for a time period that is based on the temperature readings from temperature sensors 44 and 154. In some of these embodiments, controller 66 may continue to close valve 150 until the temperature readings from reservoir temp sensor 154 and outlet temp sensor 44 come within a predetermined range of each other. In still other embodiments, other criteria may be used for determining how long to keep reservoir valve 150 closed. Regardless of the criteria used, controller 66 passes back to step 164 after opening reservoir valve 150.

Algorithm 160 may be more easily understood with respect to an example, such as the example of FIG. 6. As noted previously, FIG. 6 illustrates the results of one example of algorithm 98; however, the graphs shown in FIG. 6 can be used to illustrate how controller 66 would react to the temperatures shown in FIG. 6. As shown therein, the fluid both inside reservoir 32' and in circulation channel 36 initially starts (time $T_0$) at a temperature that, in most situations will be room temperature ($R_T$). In the example shown in FIG. 6, controller 66 starts to cool the fluid in circulation channel 36 after the thermal therapy starts and continues to cool the fluid until time $T_1$. From the initiation of the thermal therapy until time $T_1$, the fluid in reservoir 32' will not assist in the thermal treatment of the patient. This is because the residual fluid in reservoir 32' remains substantially at room temperature from time $T_0$ until time $T_1$, and the mixing of this residual fluid with the circulating fluid would only cause the circulating fluid to warm up, which is undesired during the time period from $T_0$ to $T_1$.

When time $T_1$ is reached in the example of FIG. 6, controller 66, when following algorithm 160, may determine that mixing the residual fluid with the circulating fluid would assist in the thermal therapy of the patient. This is because at time $T_1$ controller 66 begins warming the circulating fluid and the residual fluid is at a warmer temperature (room temperature) than the circulating fluid. Thus, the mixing of the residual fluid would cause a faster increase in the temperature of the circulating fluid. Controller 66 may therefore determine that such a faster increase in the temperature of the circulating fluid is desirable. This determination may be based on other factors as well, as will be discussed more below. At any point between $T_1$ and $T_{12}$, controller 66 may mix the residual fluid with the circulating fluid. However, after time $T_{12}$, controller 66 will not mix the residual fluid with the circulating fluid because the residual fluid will be colder than the circulating fluid and controller 66 is attempting to heat the fluid at that time.

After time $T_{12}$, controller 66 will not mix the residual fluid with the circulating fluid for at least as long as it takes for controller 66 to heat the circulating fluid to the desired temperature 78. Once at the desired temperature, controller 66 will again consider mixing the residual fluid with the circulating fluid at step 168 if controller 66 determines that the temperature of the fluid needs to be decreased. This is because the temperature of the residual fluid will be lower than the temperature of the circulating fluid after it has reached its maximum, and releasing the residual fluid at any time before the circulating fluid needs to be cooled would only add to the work of heat exchanger 40 and delay the arrival of the fluid at target temperature 78.

The potential times at which mixing residual fluid with circulating fluid are therefore limited to times when the residual fluid is closer to the target fluid temperature 78 than the current temperature 76 of the circulating fluid. During those times, controller 66 may close valve 150, or it may decide not to close valve 150. In making this determination, controller 66 examines, in at least some embodiments, the rate at which the temperature of the circulating fluid 76 is changing, the amount of error that has accumulated in the integral term of the control loop 74a, and/or other factors. Controller 66 may also utilize other factors in making this determination.

Controller 66 may also, or alternatively, control reservoir valve 150 in order to help avoid or reduce overshoot. For example, in the exemplary graph of FIG. 6, at the time the patient's temperature reaches target temperature 88 the second time ($T_5$), the temperature of the circulating fluid 76 is above the patient target temperature. It may therefore be desirable to quickly adjust the temperature of the circulating fluid downward so that the patient's temperature does rise above target temperature 88 (overshoot it). At time $T_5$ (or in the moments before), controller 66 may therefore mix the residual fluid with the circulating fluid in order to more quickly drop the temperature of the circulating fluid.

The selective shifting of reservoir 32' into and out of circulation channel 36 may be carried out in one of two ways, depending upon the particular embodiment of thermal control unit 22' being implemented. In the embodiment of thermal control unit 22' described above, thermal control unit 22' does not actively change the temperature of the residual fluid inside of reservoir 32'. In an alternative embodiment, which will now be described, thermal control unit 22' includes a heat exchanger 156 positioned inside reservoir 32' (or in a location close enough to thermal reservoir 32' to allow heat to be exchanged between the residual fluid inside reservoir 32' and heat exchanger 156. Heat exchanger 156 is under the control of controller 66 and includes a heater adapted to heat the temperature of the residual fluid at certain times. More specifically, controller 66 controls the heater of heat exchanger 156 such that the residual fluid inside reservoir 32' is heated when a patient's temperature is being cooled. This enables controller 66 to abruptly increase the temperature of the circulating fluid at a desired moment—such as at or near the time the patient arrives at the patient target temperature—by closing reservoir valve 150 and allowing the heated residual fluid inside reservoir 32' to mix with the circulating fluid.

In some embodiments, heat exchanger 156 also includes a chiller adapted to chill the temperature of the residual fluid inside of reservoir 32'. In such embodiments, controller 66 controls the chiller of heat exchanger 156 such that the residual fluid inside reservoir 32' is cooled when a patient's temperature is being warmed. This enables controller 66 to abruptly decrease the temperature of the circulating fluid at a desired moment—such as at or near the time when the patient arrives at the patient target temperature—by closing reservoir valve 150 and allowing the chilled residual fluid inside reservoir 32' to mix with the circulating fluid.

The heating and/or cooling of fluid inside reservoir 32' helps controller 66 abruptly change the temperature of the circulating fluid, which is particularly useful in situations where the patient is arriving at, or near to arriving at, the patient target temperature. By abruptly changing the temperature of the circulating fluid at these moments, controller 66 can help to reduce or avoid temperature overshoot. This is because, without the addition of the residual fluid to the circulating fluid at these times, it would likely otherwise take additional time to change the temperature of the fluid to the desired fluid temperature, and during that transition period, the temperature of the patient may continue to move beyond the target patient temperature.

It will be understood that, although FIG. 9 illustrates thermal control unit 22' with heat exchanger 156, heat exchanger 156 may be omitted in some embodiments of thermal control unit 22. Further, when heat exchanger 156 is included, it may be implemented solely as a chiller, solely as a heater, or as a combination of both a heater and a chiller. Still further heat exchanger 156—whether implemented as a heater, a chiller, or both—may be added to any of the other embodiments of the thermal control units described herein.

The physical form of heat exchanger 156 may take on a variety of different forms. In some embodiments, heat exchanger 156 is built into removable reservoir 32' and includes electrical contacts that come into electrical communication with contacts contained within thermal control unit 22' when reservoir 32' is inserted into thermal control unit 22'. The electrical contacts allow controller 66 to control and/or power heat exchanger 156. In other embodiments, heat exchanger is inserted into reservoir 32', but is removable therefrom (as well as from thermal control unit 22'). In still other embodiments, heat exchanger 156 is attached to a movable arm that a user moves out of the way when adding or removing reservoir 32' to or from thermal control unit 22'. When reservoir 32' is seated within thermal control unit 22', the arm is moved such that heat exchanger 156 is positioned in physical contact with the fluid within reservoir 32'. In still other embodiments, heat exchanger 156 is built into thermal control unit 22' in a stationary manner and exchanges heat with the residual fluid by having the heat pass through one or more of the walls of reservoir 32'.

Figure 11:
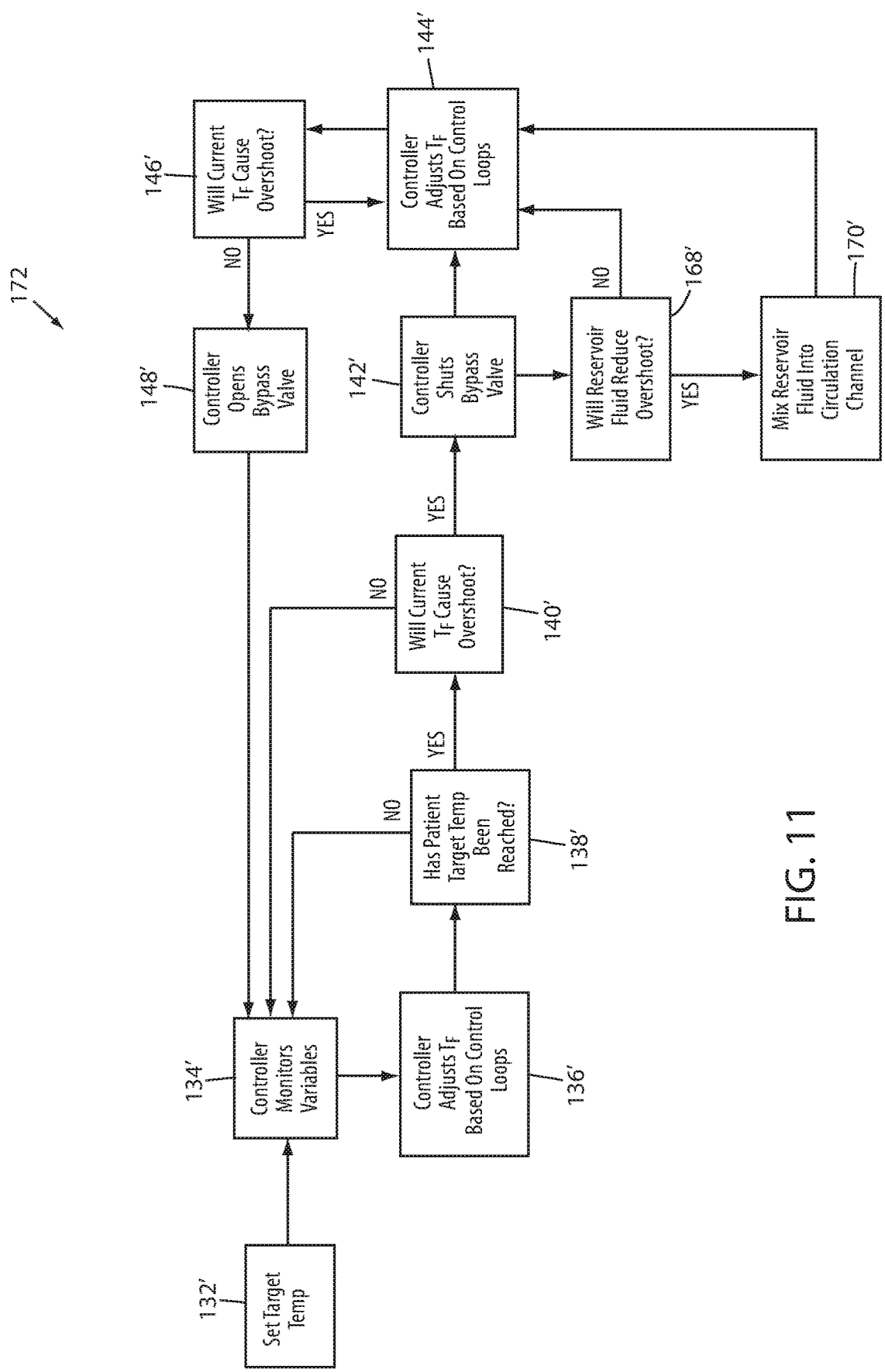
FIG. 11 is a flow diagram of a fourth temperature control algorithm that may be followed by a controller of the thermal control unit of FIG. 9.

FIG. 11 illustrates another example of a temperature control algorithm 172 that may be utilized by controller 66 of thermal control unit 22'. Algorithm 172 illustrates one manner in which algorithms 130 and 160 may be combined together. Other manners are, of course, possible. In the manner illustrated in FIG. 11, steps 132', 134', 136', 138', 140', 142', 144', 146', and 148' are the same as steps 132, 134, 136, 138, 140, 142, 144, 146, and 148, respectively, of algorithm 130 of FIG. 8. Similarly, steps 168' and 170' are the same as steps 168 and 170 of the algorithm 160 of FIG. 10. Step 168' is reached after controller 66 performs step 142' and shuts the bypass valve 56, thereby shutting off further flow to the thermal pads 24. After shutting off bypass valve 56, controller 66 determines if the residual fluid in the reservoir 32' (which may be actively heated, actively cooled, or left alone) will reduce any overshoot or not. If the answer is no, controller 66 returns to steps 144' and continues to operate in the manner previously described for step 144 of algorithm 130. If controller 66 determines that the residual fluid in the reservoir 32' will help to reduce or eliminate any overshoot, controller 66 proceeds to step 170' and mixes the residual fluid with the circulating fluid. This is done by closing reservoir valve 150. Reservoir valve 150 remains closed for any of the time periods discussed above. After step 170', controller 66 returns to step 144' and proceeds in the same manner discussed above with respect to step 144 and algorithm 130.

Algorithm 172 adds to algorithm 130 by having controller 66 assess whether the mixing of the residual reservoir fluid with the circulating fluid will expedite moving the temperature of the circulating fluid more quickly to its target temperature. As noted previously, algorithm 130 is designed to stop delivering fluid to thermal pads 24 if the temperature of the circulating fluid is such that further delivery of that fluid to the thermal pads 24 will exacerbate the patient's overshoot. When cutting off fluid delivery to thermal pads 24, algorithm 130 warms or cools the circulating fluid until it reaches a temperature that will no longer exacerbate temperature overshoot, at which point fluid delivery to thermal pads 24 resumes. Algorithm 172 expedites the internal heating or cooling of the fluid by, when appropriate, mixing the residual fluid with the circulating fluid in order to change the temperature of the circulating fluid more quickly, thereby reducing the time during which fluid is not delivered to thermal pads 24.

Figure 12:
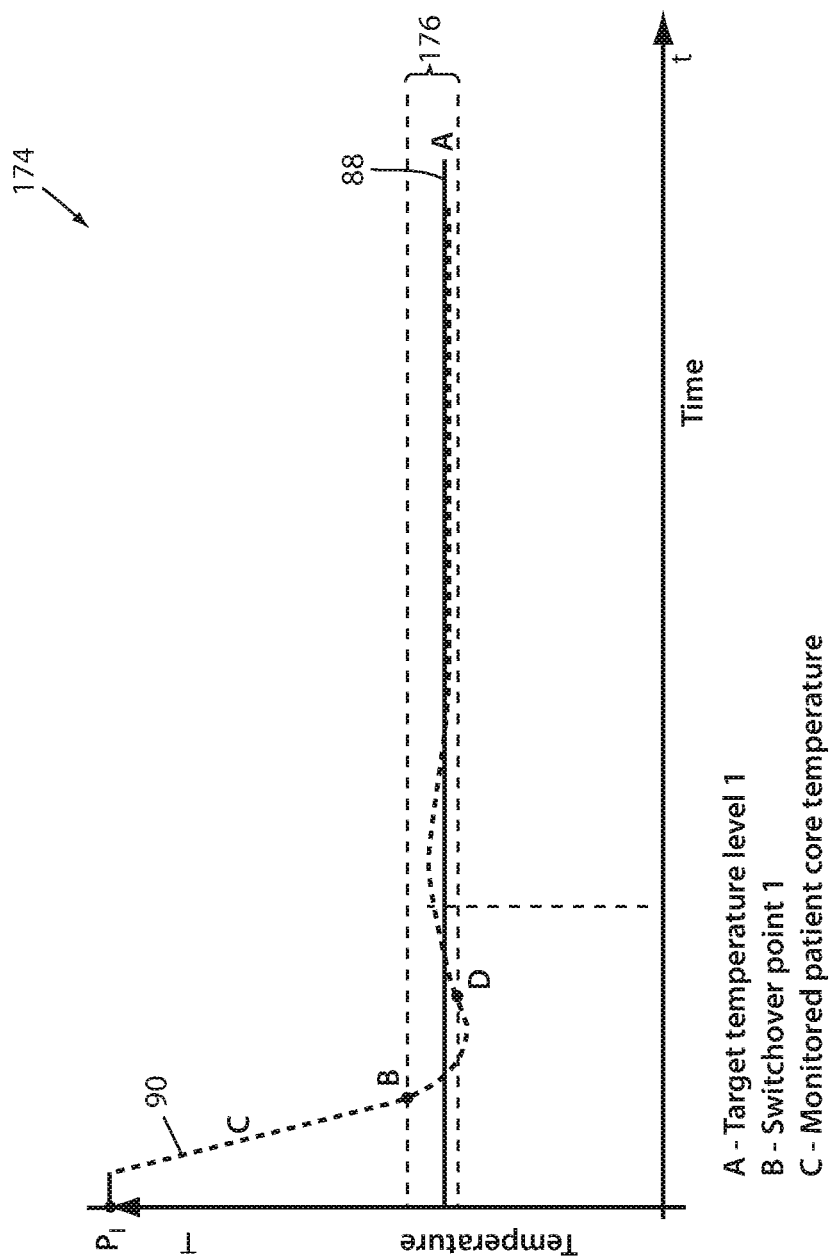
FIG. 12 is a graph of patient target temperature, patient measured temperature, and fluid temperature illustrating an example of a fifth temperature control algorithm that may be followed by the thermal control units of FIG. 3 and/or FIG. 9.

FIG. 12 illustrates an example of a graph 174 of a patient's temperature, fluid temperature, and a target patient temperature when controller 66 of either thermal control unit 22 or 22' is operating according to yet another temperature control algorithm. In the temperature control algorithm of FIG. 12, controller 66 uses control loops 74a and 74b (or modifications thereto) to control the temperature of the circulating fluid and the automatically adjust the temperature of a patient toward target temperature 88. The algorithm of FIG. 12 differs from the previously described algorithms in that controller 66 utilizes different coefficients in the control loops 74a and 74b at different points during the thermal treatment. The use of different coefficients at different time periods helps to achieve the patient's target temperature more quickly, yet with a reduced (or absent) amount of overshoot.

As with the other algorithms described herein, the patient's temperature begins at an initial temperature $P_I$. After thermal therapy starts, the temperature of the fluid circulating to the thermal pads 24 is reduced, and the patient's temperature 90 is adjusted toward patient target temperature 88. When the patient's temperature first falls within a range 176 of the target temperature 88, signified by point B in FIG. 12, controller 66 switches to using a different set of coefficients for at least one of control loops 74a and 74b. In some embodiments, controller 66 performs the switchover at point B to a different set of coefficients only if one or more criteria are met at or near the time of point B. For example, in some embodiments, controller 66 analyzes the accumulated error in the integral term of either or both of control loops 74a and 74b and switches to a different set of coefficients if the integral error has accumulated to a value greater than a threshold. If the integral error has not accumulated to more than the threshold, controller 66 continues to use the same set of coefficients. In other embodiments, other thresholds may be used for one or more different criteria.

The time (point B in FIG. 12) at which the coefficient transition, if any, occurs may be based on several variables. In some embodiments, point B may be selected using the same criteria as point $T_A$ discussed above with respect to algorithm 98. In some embodiments, point B may be chosen as a patient temperature that corresponds to a predefined fraction of the difference between the patient's initial temperature ($P_I$) and the target temperature. In still other embodiments, point B may be chosen based on the slope of the patient's temperature and a prediction of when the patient's temperature will arrive at the target temperature 88. In these latter embodiments, point B may be selected as a predefined amount of time before the patient target temperature 88 is predicted to be achieved, given the recent slope of the patient's temperature changes. Still other criteria may be used.

After switching to a different set of coefficients at point B, controller 66 continues to use the newly selected coefficients until after the patient's temperature has reached target temperature 88. After reaching target temperature 88, controller 66 re-assesses the coefficients at point D in FIG. 12. Point D refers to a time at which the patient's temperature has returned, after exiting, to within the defined range 176 of the target temperature 88. At point D, controller 66 once again re-assesses the current slope of the patient's temperature, the current error in the patient's temperature (difference between target temperature 88 and the patient's current temperature), and potentially other variables (e.g. the accumulated error in the integral terms of loops 74a and/or 74b). Controller 66 then decides whether to switch to using different coefficients or not. When switching to different coefficients, the different coefficients may be the same as those previously used prior to point B, or they may be coefficients that are completely new, or a blend of the two. In some embodiments, the coefficients are selected based on the current error value in the patient's temperature. For example, the derivative coefficient (if a derivative term is used) may be based on the current value of the derivative term, the proportional coefficient (if a proportional term is used) may be based on the current error value in the patient's temperature, and the integral coefficient (if an integral term is used) may be based on the current value of the integral term. Other factors may also be used to select and/or calculate one or more new coefficients.

Although not illustrated in FIG. 12, one or more assessment points after point D may exist where controller 66 again assesses whether or not to change the coefficients used in control loops 74a and/or 74b. These may occur each time the patient's temperature overshoots the target temperature, or at other times. As with all of the changes to the coefficients, any new coefficients are selected in order to reduce overshoot and/or the magnitude of oscillations about the target temperature 88.

In some embodiments, the new coefficients that are used are chosen based upon the rate at which the patient's temperature is approaching the patient target temperature 88. If, for example, the rate of change of the patient's temperature is steep in the vicinity of the target temperature 88 such that it is likely that the patient's temperature will overshoot the target temperature 88 a relatively large amount (as predicted at an assessment point, such as points B or D), controller 66 selects a new gain coefficient that has a smaller value. On the other hand, if the rate of change of the patient's temperature is too shallow when in the vicinity of the target temperature 88 such that it is likely that the patient's target temperature will not be reached in a relatively short time, controller 66 selects a new gain coefficient that has a larger value.

It will be understood that, in some embodiments, the number of assessment points reached by controller 66 will vary in response to the reaction of the patient undergoing thermal treatment. Thus, for example, in those embodiments where range 176 is defined as a predefined range around the patient target temperature 88, controller 66 may only reach an assessment point (point B in FIG. 12) once. This is particularly true where, after reaching the first assessment point, the patient's temperature remains within a tighter range of the target temperature 88 than range 176. In other words, if the patient's temperature never ventures outside of range 176 after point B, then point D (and any future assessment points) may never occur for that particular thermal treatment session. Therefore, the number of times controller 66 switches coefficients may vary in response to the particular patient undergoing thermal treatment and his or her reaction to the thermal treatment.

It will be understood that, although the algorithm illustrated in FIG. 12 has been described herein as a separate algorithm, it may be mixed with any of the algorithms 98, 130, 160, and/or 172 previously described. Alternatively, of course, the algorithm of FIG. 12 may be used separately and without any of algorithms 98, 130, 160, and 172. It will also be understood that the algorithm of FIG. 12 may be used with both thermal control unit 22 and thermal control unit 22', as well as other types of thermal control units. It will also be understood that, although algorithms 98 and 130 have been described herein as being used with thermal control unit 22, either or both of these algorithms may be used with thermal control unit 22' as well. Still further, any of the temperature control algorithms disclosed herein may be used individually, or combined with any one or more of the other algorithms disclosed herein.

Various modifications may also or alternatively be made to the physical construction of thermal control units 22 and/or 22' beyond those described above. For example, the particular order of the components along circulation channel 36 of control units 22, 22' may also or alternatively be varied from what is shown in the drawings. For example, although the drawings depict pump 34 as being upstream of heat exchanger 40, and air remover 58 as being upstream of pump 34, this order may be changed. Air remover 58, pump 34, heat exchanger 40 and reservoir 32 (or 32') may be positioned at any suitable location along circulation channel 36.

Bypass valve 56 may also be implemented as a conventional check valve that automatically opens to allow fluid to flow through bypass line 52 when the pressure in circulation channel 36 exceeds a particular pressure. In order to control the flow of fluid through bypass line 52, an additional valve may be positioned between bypass valve 56 and outlet manifold 42 that is controllable by controller 66. When controller 66 shuts this additional valve, the fluid pressure within circulation channel 36 adjacent bypass valve 56 builds up until valve 56 opens and fluid is allowed to flow through bypass line 52. Still other manners of controlling the flow of fluid through bypass line 52 may also be implemented.

When carrying out any of the aforementioned temperature control algorithms 98, 130, 160, and/or 172, controller 66 may also be configured to make one or more adjustments to condenser 47 (if included; see FIG. 3 and FIG. 9) within thermal control unit 22 or 22', and/or fan 51 that blows heat away from the condenser 47 (in an air cooled condenser), and/or a speed of compressor 45. In a liquid cooled condenser, fan 51 may be replaced by an impeller that pumps liquid past the condenser 47 to remove the heat from the chiller 41, and the speed of the impeller may be adjusted. The adjustments to condenser 47, the fan 51 (or impeller), and the compressor 45 are made to alter the cooling power of the chiller 41. Such adjustments may be made in any of the manners disclosed in commonly assigned U.S. patent application Ser. No. 62/477,596 filed Mar. 28, 2017, by inventors Gregory Taylor et al. and entitled THERMAL SYSTEM, the complete disclosure of which is incorporated herein by reference. In addition to, or in lieu of, such adjustments to the compressor 45, condenser 47, and/or fan 51, controller 66 may also be modified in any of the thermal control units discussed herein to change a flow rate of the circulating fluid delivered to thermal pads 24.

In any of the embodiments of thermal control unit 22' discussed herein, controller 66 may also or alternatively be configured to selectively open and close reservoir valve 150 in order to facilitate the cleaning and/or disinfection of thermal control unit 22'. In such embodiments, controller 66 may be programmed to close (and open) reservoir valve 150 during routine maintenance of thermal control unit 22' and/or during cleansing and/or disinfecting cycles of thermal control unit 22'. By closing and opening reservoir valve 150 during a cleansing or disinfection cycle, cleansing agents within the circulating fluid are not only carried throughout circulation channel 36 (when valve 150 is open), but they are also carried through reservoir 32' (when valve 150 is closed). By closing valve 150 for at least a portion of the disinfection/cleansing cycle, personnel do not need to remove reservoir 32' and clean or disinfect it by hand. Instead, the cleansing/disinfection can be carried out automatically without the user having to take any special steps with respect to reservoir 32'. The selective opening and closing of reservoir valve 150 during cleansing/disinfection cycles may be carried out in conjunction with any of the cleansing/disinfection techniques disclosed in commonly assigned U.S. patent application Ser. No. 62/406,676 filed Oct. 11, 2016, by inventors Marko Kostic et al. and entitled THERMAL CONTROL SYSTEM, the complete disclosure of which is hereby incorporated herein by reference. It may also be used with still other cleansing/disinfection techniques.

Various other alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A thermal control unit for controlling a patient's temperature, the thermal control unit comprising:
   a fluid outlet adapted to fluidly couple to a fluid supply line;
   a fluid inlet adapted to fluidly couple to a fluid return line;
   a circulation channel coupled to the fluid outlet and the fluid inlet;
   a pump for circulating fluid through the circulation channel from the fluid inlet to the fluid outlet;
   a heat exchanger adapted to add or remove heat from the fluid circulating in the circulation channel when activated;
   a fluid temperature sensor adapted to sense a temperature of the fluid;
   a patient temperature probe port adapted to receive patient temperature readings from a patient temperature probe;
   a user interface adapted to receive a patient target temperature; and
   a controller in communication with the patient temperature probe port, the pump, the fluid temperature sensor, and the user interface, the controller adapted to stop a flow of fluid out of the fluid outlet prior to the patient temperature reaching the patient target temperature, wherein the controller is adapted to monitor a slope of the patient temperature readings after the flow of fluid out of the fluid outlet is stopped for a predefined time period, and to restart the flow of fluid out of the fluid outlet after the predefined time period if the slope of the patient temperature readings changes by more than a threshold.

2. The thermal control unit of claim 1 wherein the controller, after restarting the flow of fluid out of the fluid outlet, is adapted to re-stop the flow of fluid out of the fluid outlet after the patient temperature has moved toward the patient target temperature but prior to the patient temperature reaching the patient target temperature.

3. The thermal control unit of claim 1 wherein, if the slope of the patient temperature readings does not change by more than the threshold during the predefined time period, the controller is adapted to activate the pump and close a valve such that the fluid circulates within the circulation channel of the thermal control unit but does not flow out of the fluid outlet, wherein the controller is further adapted to activate the heat exchanger while the valve is closed until the temperature of the fluid reaches a specific temperature.

4. The thermal control unit of claim 3 wherein the controller is adapted to open the valve after the temperature of the fluid reaches the specific temperature.

5. A thermal control unit for controlling a patient's temperature, the thermal control unit comprising:
   a fluid outlet adapted to fluidly couple to a fluid supply line;
   a fluid inlet adapted to fluidly couple to a fluid return line;
   a circulation channel coupled to the fluid outlet and the fluid inlet;
   a pump for circulating fluid through the circulation channel from the fluid inlet to the fluid outlet;
   a heat exchanger adapted to add or remove heat from the fluid circulating in the circulation channel when activated;
   a fluid temperature sensor adapted to sense a temperature of the fluid;
   a patient temperature probe port adapted to receive patient temperature readings from a patient temperature probe;
   a user interface adapted to receive a patient target temperature; and
   a controller in communication with the patient temperature probe port, the pump, the fluid temperature sensor, and the user interface, the controller adapted to stop a flow of fluid out of the fluid outlet prior to the patient temperature reaching the patient target temperature; wherein the controller is adapted to stop the flow of fluid out of the fluid outlet by closing a valve to the fluid outlet, and the controller is further adapted to continue to activate the pump such that fluid is pumped internally within the circulation channel while the flow of fluid out of the fluid outlet is stopped.

6. A thermal control unit for controlling a patient's temperature, the thermal control unit comprising:
   a fluid outlet adapted to fluidly couple to a fluid supply line;
   a fluid inlet adapted to fluidly couple to a fluid return line;
   a circulation channel coupled to the fluid outlet and the fluid inlet;
   a pump for circulating fluid through the circulation channel from the fluid inlet to the fluid outlet;
   a heat exchanger adapted to add or remove heat from the fluid circulating in the circulation channel when activated;

a fluid temperature sensor adapted to sense a temperature of the fluid;

a patient temperature probe port adapted to receive patient temperature readings from a patient temperature probe;

a user interface adapted to receive a patient target temperature; and a controller in communication with the patient temperature probe port, the pump, the fluid temperature sensor, and the user interface, the controller adapted to stop a flow of fluid out of the fluid outlet prior to the patient temperature reaching the patient target temperature; wherein the controller is adapted to control the heat exchanger using first and second control loop feedback mechanisms, the first control loop feedback mechanism using a first set of coefficients and an error value, the second control loop feedback mechanism using a second set of coefficients and the error value, and the error value being defined as a difference between a current patient temperature reading and the patient target temperature.

7. A thermal control unit for controlling a patient's temperature, the thermal control unit comprising:

a fluid outlet adapted to fluidly couple to a fluid supply line;

a fluid inlet adapted to fluidly couple to a fluid return line;

a circulation channel coupled to the fluid outlet and the fluid inlet;

a pump for circulating fluid through the circulation channel from the fluid inlet to the fluid outlet;

a heat exchanger adapted to add or remove heat from the fluid circulating in the circulation channel when activated;

a fluid temperature sensor adapted to sense a temperature of the fluid;

a patient temperature probe port adapted to receive patient temperature readings from a patient temperature probe;

a user interface adapted to receive a patient target temperature; and a controller in communication with the patient temperature probe port, the pump, the fluid temperature sensor, and the user interface, the controller adapted to deactivate the heat exchanger prior to the patient temperature reaching the patient target temperature such that the heat exchanger does not actively add heat to, or remove heat from, the fluid, wherein the controller is adapted to monitor a slope of the patient temperature readings for a predefined time period after deactivating the heat exchanger and to reactivate the heat exchanger after the predefined time period if the slope of the patient temperature readings changes by more than a threshold.

8. The thermal control unit of claim 7 wherein the controller, after reactivating the heat exchanger, is adapted to deactivate the heat exchanger again after the patient temperature has moved toward the patient target temperature but prior to the patient temperature reaching the patient target temperature.

9. The thermal control unit of claim 7 wherein, if the slope of the patient temperature readings does not change by more than the threshold during the predefined time period, the controller is adapted to activate the pump and close a valve such that the fluid circulates within the circulation channel of the thermal control unit but does not flow out of the fluid outlet.

10. The thermal control unit of claim 9 wherein the controller is further adapted to reactivate the heat exchanger while the valve is closed until the temperature of the fluid reaches a specific temperature and to open the valve after the temperature of the fluid reaches the specific temperature.

11. A thermal control unit for controlling a patient's temperature, the thermal control unit comprising:

a fluid outlet adapted to fluidly couple to a fluid supply line;

a fluid inlet adapted to fluidly couple to a fluid return line;

a circulation channel coupled to the fluid outlet and the fluid inlet;

a pump for circulating fluid through the circulation channel from the fluid inlet to the fluid outlet;

a heat exchanger adapted to add or remove heat from the fluid circulating in the circulation channel when activated;

a fluid temperature sensor adapted to sense a temperature of the fluid;

a patient temperature probe port adapted to receive patient temperature readings from a patient temperature probe;

a user interface adapted to receive a patient target temperature; and a controller in communication with the patient temperature probe port, the pump, the fluid temperature sensor, and the user interface, the controller adapted to control the heat exchanger to bring the patient to the patient target temperature using first and second control loop feedback mechanisms, the first control loop feedback mechanism using a first set of coefficients and an error value, and the second control loop feedback mechanism using a second set of coefficients and the error value, wherein the error value is defined as a difference between a current patient temperature reading and the patient target temperature reading.

12. The thermal control unit of claim 11 wherein the first control loop feedback mechanism includes first proportional, first integral, first derivative control terms, each of which is multiplied by a coefficient from the first set of coefficients, and the second control loop feedback mechanism includes second proportional, second integral, and second derivative control terms, each of which is multiplied by a coefficient from the second set of coefficients.

13. The thermal control unit of claim 11 wherein the controller is further adapted to vary a flow of the fluid exiting the fluid outlet when bringing the patient to the patient target temperature, and to switch from using the first control loop feedback mechanism to using the second control loop feedback mechanism at a transition point, the transition point occurring prior to the patient reaching the patient target temperature.

14. The thermal control unit of claim 12 wherein the controller switches from using the first control loop feedback mechanism to using the second control loop feedback mechanism at a transition point, the transition point occurring after the patient reaches the patient target temperature.

15. The thermal control unit of claim 11 wherein the controller is further adapted to control the heat exchanger to bring the patient to the patient target temperature using a third control loop feedback mechanism, the third control loop feedback mechanism using a third set of coefficients and the error value, and wherein the third control loop feedback mechanism includes proportional, integral, derivative control terms, each of which is multiplied by a coefficient from the third set of coefficients.

16. The thermal control unit of claim 15 wherein the controller is adapted to switch from using the first control loop feedback mechanism to using the second control loop feedback mechanism at a first transition point, and to switch from using the second control loop feedback mechanism to using the third control loop feedback mechanism at a second transition point, the first transition point occurring prior to the patient reaching the patient target temperature and the second transition point occurring after the patient reaches the patient target temperature.

17. The thermal control unit of claim 11 further comprising:
- a fluid reservoir adapted to supply fluid to the circulation channel; and
- a valve adapted to selectively include the fluid reservoir in the circulation channel and selectively exclude the fluid reservoir from the circulation channel, the fluid flowing through the fluid reservoir when the fluid reservoir is included in the circulation channel and the fluid flowing around the fluid reservoir when the fluid reservoir is excluded from the circulation channel;
- wherein the controller is adapted to control the temperature of the fluid in the circulation channel using both the heat exchanger and the valve.

18. The thermal control unit of claim 17 further comprising a second heat exchanger adapted to add or remove heat to fluid contained within the fluid reservoir such that a temperature of the fluid inside of the fluid reservoir can be adjusted independently of the fluid outside of the fluid reservoir.

* * * * *